US007771959B2

(12) United States Patent
Beall et al.

(10) Patent No.: US 7,771,959 B2
(45) Date of Patent: Aug. 10, 2010

(54) METHODS TO DETERMINE THE PRESENCE OR AMOUNT OF CANINE PANCREATIC LIPASE WITH ANTIBODIES

(75) Inventors: Melissa Beall, Cape Elizabeth, ME (US); Stacey Pazar Huth, Portland, ME (US); Eugene Regis Krah, Freeport, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 585 days.

(21) Appl. No.: 11/107,086

(22) Filed: Apr. 15, 2005

(65) Prior Publication Data

US 2005/0233368 A1 Oct. 20, 2005

Related U.S. Application Data

(60) Provisional application No. 60/564,333, filed on Apr. 22, 2004, provisional application No. 60/562,836, filed on Apr. 16, 2004.

(51) Int. Cl.
*G01N 33/53* (2006.01)
(52) U.S. Cl. .................................. 435/7.4; 435/7.1
(58) Field of Classification Search .................. None
See application file for complete search history.

(56) References Cited

U.S. PATENT DOCUMENTS

| | | | | |
|---|---|---|---|---|
| 4,486,530 | A | * | 12/1984 | David et al. ............... 435/7.91 |
| 4,555,483 | A | | 11/1985 | LiMuti et al. |
| 4,845,028 | A | | 7/1989 | Imamura et al. |
| 4,948,723 | A | * | 8/1990 | Hermon-Taylor et al. .. 435/7.92 |
| 5,093,256 | A | | 3/1992 | Shen et al. |
| 5,173,417 | A | | 12/1992 | Takeda et al. |
| 5,219,753 | A | | 6/1993 | Berka et al. |
| 5,232,846 | A | | 8/1993 | Takeda et al. |
| 5,244,798 | A | | 9/1993 | Takeda et al. |
| 5,248,598 | A | | 9/1993 | Kwan et al. |
| 5,328,832 | A | | 7/1994 | Miki et al. |
| 5,378,609 | A | | 1/1995 | Kwan et al. |
| 5,449,607 | A | | 9/1995 | Wilton |
| 5,750,333 | A | | 5/1998 | Clark et al. |
| 5,849,296 | A | | 12/1998 | Navia et al. |
| 5,976,529 | A | | 11/1999 | Navia et al. |
| 6,004,768 | A | | 12/1999 | Navia et al. |
| 6,074,863 | A | | 6/2000 | Svendsen et al. |
| 6,297,014 | B1 | | 10/2001 | Taylor et al. |
| 6,322,993 | B1 | | 11/2001 | Schelong et al. |
| 6,337,187 | B1 | | 1/2002 | Kapeller-Libermann |
| 6,558,936 | B1 | | 5/2003 | Khodadoust et al. |
| 6,682,903 | B2 | * | 1/2004 | Saunders .................. 435/7.92 |
| 6,797,502 | B2 | | 9/2004 | Kapeller-Libermann |
| 6,855,506 | B2 | | 2/2005 | Steiner et al. |
| 6,864,064 | B2 | | 3/2005 | Kapeller-Libermann |
| 2002/0052034 | A1 | * | 5/2002 | Guegler et al. ............. 435/198 |
| 2003/0207333 | A1 | | 11/2003 | Steiner et al. |

OTHER PUBLICATIONS

Campbell, A. (Monoclonal Antibody Technology [1985] pp. 1-32.*
Aoubala et al., J. Biol. Chem. 270: 3932-3937, 1995.*
DeCaro, Josiane, et al., *Pancreatic lipase-related protein 1 (PLRP1) is present in the pancreatic juice of several species*, Biochemie et Biophysica Acta, 1387:331-341 (1998).
Tan, S.W., et al., *Production and Characterization of Murine Monoclonal Antibodies to Blastocystis hominis*, International Journal for Parasitology, 26(4):375-381 (1996).
Aoubala, Mustapha, et al., *Human Pancreatic Lipase*, The Journal of Biological Chemistry, 270(8):3932-3937 (1995).
Visai, Livia, et al., *Identification and characterization of a new ligand-binding site in FnbB, a fibronection-binding adhesion from Streptococcus dysgalactiae*, Biochimica et Biophysica Acta 1646:173-183 (2003).
Lowe, et al., *Cloning and Characterization of Human Pancreatic Lipase cDNA*, Journal of Biological Chemistry, 264(33):20042-20048 (1989).
Mickel, F. Susan, et al., *Structure of the Canine Pancreatic Lipase Gene*, The Journal of Biological Chemistry, 264:12895-12901 (1989).
Quigley, et al., *Hyperlipasemia in 6 Dogs with Pancreatic or Hepatic Neoplasia: Evidence for Tumor Lipase Production*, Veterinary Clinical Pathology, 30:114-120 (2001).
Peterson, et al., *A sequence analysis of lipases, esterases and related proteins*, Lipases—their structure, biochemistry and application, Woolley, P. and Peterson, S., eds., Cambridge University Press, pp. 23-48 (1994).
Lin, et al., *Substrate Specificities of Lipases from Corn and Other Seeds*, Archives of Biochemistry and Biophysics, 244:346-356 (1986).
Jaeger, et al., *Bacterial lipases*, FEMS Microbiology Reviews, 15:29-63 (1994).
Mukherjee, K.D., et al., *Lipases from plants*, Lipase—their structure, biochemistry and application, Woolley, P. and Peterson, S., eds., Cambridge University Press, pp. 49-75 (1994).

(Continued)

*Primary Examiner*—Phillip Gambel
(74) *Attorney, Agent, or Firm*—McDonnell Boehnen Hulbert & Berghoff LLP

(57) ABSTRACT

Isolated nucleic acid molecules having a nucleotide sequence encoding canine pancreatic lipase polypeptides, allelic variants and fragments thereof. Vectors and host cells containing the polynucleotide sequences and methods for expressing the polypeptides. Monoclonal antibodies that specifically binds to the canine pancreatic lipase polypeptides. Cell lines secreting the monoclonal antibodies. Methods for determining the presence or amount of canine pancreatic lipase in a biological sample. The methods include using the monoclonal antibodies to specifically bind to canine pancreatic lipase polypeptides. The method includes using standards of recombinant canine pancreatic lipase. Devices and kits for performing methods for detecting canine pancreatic lipase in biological samples.

17 Claims, 11 Drawing Sheets

OTHER PUBLICATIONS

Lawson, David, et al., *The three-dimensional structures of two lipases from filamentous fungi*, Lipase—their structure, biochemistry and application, 77-94 (1994).

Svendsen, Allan, *Sequence comparisons within the lipase family*, Lipase—their structure, biochemistry and application, Woolley, P. and Peterson, S., eds., Cambridge University Press, pp. 1-21 (1994).

Antonian, Edna, *Recent Advances in the Purification, Characterization and Structure Determination of Lipases*, Lipids, 23:1101-1106 (1988).

Carrière, Frédéric, *Molecular evolution of the pancreatic lipase and two related enzymes towards different substrate selectivities*, Journal of Molecular Catalysis B: Enzymatic, 3:55-64 (1997).

Carrière, Frédéric, *Structural basis for the substrate selectivity of pancreatic lipases and some related proteins*, Biochimica et Biophysica Acta, 1376:417-432 (1998).

Hirata, Ken-ichi, et al., *Cloning of a Unique Lipase from Endothelial Cells Extends the Lipase Gene Family*, The Journal of Biological Chemistry, 274:14170-14175 (1999).

Anderson, Richard, et al., *Cloning and Expression of cDNA Encoding Human Lysosomal Acid Lipase/Cholesteryl Ester Hydrolase*, The Journal of Biological Chemistry, 266:22479-22484 (1991).

Carriere, Frederic, et al., *Gastric lipases: cellular, biochemical and kinetic aspects*, Lipase—their structure, biochemistry and application, Woolley, P. and Peterson, S., eds., Cambridge University Press, pp. 181-205 (1994).

Moreau, Hervé, et al., *Screening of preduodenal lipases in several mammals*, Biochimica et Biophysica Acta, 959:247-252 (1988).

Carriere, Frederic, et al., *Secretion and Contribution of Lipolysis of Gastric and Pancreatic Lipases During a Test Meal in Humans*, Gastroenterology, 105:876-888 (1993).

Carriere, Frederic, et al., *Gastric and Pancreatic Lipase Levels during a Test Meal in Dogs*, Scand J. Gastroenterol, 28:443-454 (1993).

Carriere, Frederic, et al., *Purification and biochemical characterization of dog gastric lipase*, Eur. J. Biochem, 202:75-83 (1991).

Steiner, Jorg, et al., *Cellular immunolocalization of gastric and pancreatic lipase in various tissues obtained from dogs*, American Journal of Veterinary Research, 63:722-727 (2002).

Rathelot, Joelle, et al., *Horse pancreatic lipase*, Interaction with colipase from various species, Biochimie, 63: 227-234 (1981).

Bosc-Bierne, Isabelle, et al., *Studies on Chicken Pancreatic Lipase and Colipase*, Biochimica et Biophysica Acta, 794: 65-71 (1984).

Mejdob, Hafedh, et al., *Dromedary pancreatic lipase: Purification and structural properties*, Biochimica et Biophysica Acta, 1213: 119-126 (1994).

Steiner, Jorg, et al., *Purification of classical pancreatic lipase from dog pancreas*, Biochimie 84: 1243-1251 (2002).

Steiner, Jorg, et al., *Development and analytic validation of an enzyme-linked immunosorbent assay for the measurement of canine pancreatic lipase immunoreactivity in serum*, The Canadian Journal of Veterinary Research, 67:175-182 (2003).

Steiner, Jorg, et al., *Development and validation of a radioimmunoassay for the measurement of canine pancreatic lipase immunoreactivity in serum of dogs*, American Journal of Veterinary Research, 64:1237-1241 (2003).

Kemppainen, Esko, et al., *Advances in the laboratory diagnostics of acute pancreatitis*, Ann Med, 30:169-175 (1998).

Leger, Claude, et al., *Binding Between Immobilized Anti-Colipase Purified Antibodies and Colipase*, Biochimica et Biophysica Acta, 713:208-221 (1982).

Loor, Rueyming, et al., *Purification and Characterizatoin of A Human Pancreas-Specific Antigen*, Biochimica et Biophysica Acta, 668:222-234 (1981).

Dezan, Christine, et al., *Monoclomal Antibodies to Human Pancreatic Procolipase: Production and Characterization by Competitive Binding Studies*, Hybridoma 13:509-517.

Carrere, Jaqueline, et al., *Assay of human pancreatic lipase in biological fluids using a non-competitive enzyme immunoassay*. Clinica Chimica Acta, 161:209-219 (1986).

Ohta, Tetsuo, et al., *Presence of Pancreatic α-Amylase, Trypsinogen, and Lipase Immunoreactivity in Normal Human Pancreatic Ducts*, Pancreas, 9:382-386 (1994).

Uhl, W., et al., *Determination of Pancreatic Lipase by Immunoactivation Technology*, International Journal of Pancreatology, 3:253-261 (1992).

Gieseg, S.P., et al., *The Purification of Ovine Pancreaticc Lipase that is Free of Colipase Using an Improved Delipidation Method*, Pancreas, 7:45-51 (1992).

Steiner, J.M. et al., D.A. 2001a, *Serum canine pancreatic lipase immunoreactivity (cPLI) concentrations in dogs with spontaneous pancreatitis*, J. Vet. Int. Med. 15, 274.

Steiner, J.M., et al., D.A. 2000b, *Serum canine pancreatic lipase immunoreactivity (cPLI) concentrations in dogs with exocrine pancreatic insufficiency*, J. Vet. Int. Med. 15, 274.

Steiner, J.M., et al. D.A. 2000c, *Development validation of an enzyme-linked immunosorbent assay (ELISA) for the measurement of canine pancreatic lipase immunoreactivity (cPLI) in serum*, J. Vet. Int. Med. 15, 311.

Steiner, et al., "Development and analytic validation of an enzymelinked immunosorbent assay for the measurement of canine pancreatic lipase immunoreactivity in serum", Can J. Vet Res., 2003, 67(3), pp. 175-182.

Abstract: Steiner, et al., Canine Pancreatic Lipase Immunoreactivity Test (cPLI) (Texas A & M University); www.cvm.tamu.edu; (2000).

Abstract: Pancreatic Lipase Immunoreactivity (cPLI) Test for diagnosis of pancreatitis in dogs only; GI Lab, College of Veterinary medicine, Texas A & M University; (1999).

Abstract: Steiner, et al., Development and Validation of a Radioimmunoassay for the Measurement of Canine Pancreatic Lipase Immunoreactivity (cPLI) in Serum; ACVIM Poster Abstract 201 (2000).

Confluolip™ Pancreatic Lipase Test Package Insert, www.researchd.com (2002).

* cited by examiner

FIG. 1

Primer design for 3'RACE

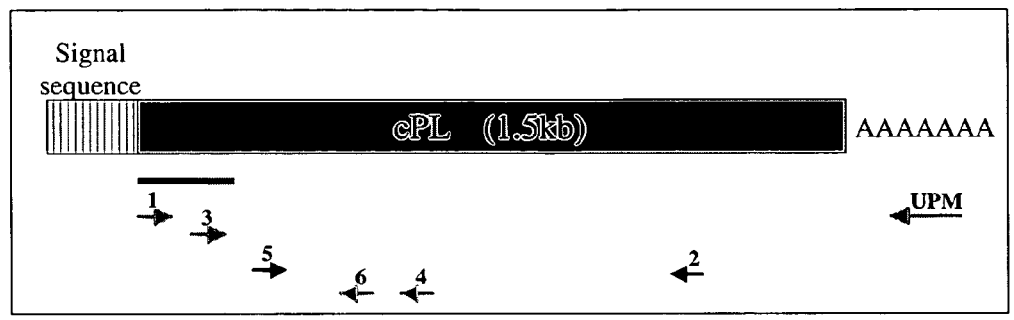

— N-terminal amino acid sequence (25) from purified protein

```
Primer 1:   5' gtggccggcaaggaggtstgyttycchmg 3'
            [SEQ ID NO:4]

Primer 2:   5' ggtgttcaggtagaacacytgbccsacbyc 3'
            [SEQ ID NO:5]

Primer 3:   5' gacgacagcccctgggcyggvatygtsga 3'
            [SEQ ID NO:6]

Primer 4:   5' ctgcccccacgatccggatgttctgcg 3'
            [SEQ ID NO:7]

Primer 5:   5' gatcctgccctggagcccbraggaygtsra 3'
            [SEQ ID NO:8]

Primer 6:   5' ctggagcttgtgataattgatggatctgc 3'
            [SEQ ID NO:9]
```

FIG. 2

Canine Pancreatic Lipase DNA Sequence (SEQ ID NO: 2)

GGTGCGTGGAACCCAACGGAACTGCCACGATGCTGCTAATCTGGACACTATC
ACTGCTGCTGGGAGCAGTAGTAGGAAAAGAAGTCTGCTTCCCAAGACTTGGC
TGTTTTAGTGATGACTCCCCATGGGCAGGAATTGTGGAGAGACCCCTCAAAA
TATTGCCCTGGGCTCCAAAAGATGTCAATACCCGCTTACTCCTATACACTAAC
GAGAACCCAGATAACTTTCAAGAACTTACTGCAGATCCATCAATTATCACAA
GCTCCAGTTTCAAAACAGATAGAAAAACCCGCTTTATTATTCATGGATTCATA
GACAAGGGAGAAGAAAGCTGGTTGGCCAACATGTGCAAGAAAATGTTTGTA
GTGGAAAGTGTGAACTGCATCTGTGTGGACTGGAAGAGTGGCTCCCGAACTG
GTTACACTCAGGCCTCGCAGAACATCCGGATCGTGGGGGCAGAAGTGGCATA
TTTTGTTGAAGTTCTTCAGTCAGCATTTGGGTACTCGCCTTCCGACGTCCACAT
CATTGGCCACAGCCTGGGAGCCCACGCAGCTGGGGAGGCAGGAAGGAGGCT
CAATGGCACTGCAGGACGAATCACAGGGTTGGATCCAGCTGAACCTTGCTTT
GAGGGCACACCCGAATTAGTCCGATTGGACCCCAGCGATGCCCAGTTTGTGG
ATGTAATTCACACAGATGCTGCCCCTATAATCCCCAACATGGGGTTTGGAATG
AGTCAAACTGTAGGCCACCTAGATTTCTTTCCAAATGGAGGAAAAGAAATGC
CTGGATGTCAGAAGAATATTCTCTCAGATTGTTGACATAGATGGGATCTGG
GAAGGGACTCGTGACTTTGTGGCCTGTAATCACTTAAGAAGTTACAAGTATT
ACTCTGATAGCATCCTCAACCCTGACGGCTTTGCTGGATTCCCTTGTGCCTCTT
ACAATGTTTTCACTGCAAACAAGTGCTTCCCCTGCCCAAGCGAAGGCTGCCC
ACAGATGGGTCATTATGCTGACAGATTTCCTGGAAAAACTGACAAAGTGAAC
CAGATATTCTATCTAGACACTGGTGATGCCAGCAATTTTGCCCGTTGGAGGTA
TAAGGTAGCTGTCACACTGTCTGGGAAGAAGGTTACAGGACACGTGCTAGTT
TCTCTGTTTGGAAATAAAGGAAATTCTAAACAGTATGAAATTTTCAAGGGCA
CTCTCCAACCAGAGAGCACTCATTCCAATGAATTTGACTCTGATGTGGAAGTT
GGAGATGTGCAGAAGGTTAAATTTGTTTGGTACAACAATGTGATCAACCCAA
CTCTACCCAGAGTGGGAGCATCCAAGATCACAGTGGAAAGAAATGATGGGA
AAATATTCAACTTCTGTAGTAAAGAAACCGTGAGGGAAGATATTTTACTTACT
CTTACCCCATGTTAAGA

FIG. 3

Canine Pancreatic Lipase amino acid sequence (SEQ ID NO: 3)

MLLIWTLSLLLGAVVGKEVCFPRLGCFSDDSPWAGIVERPLKILPWAPKDVNTRLLLYT
NENPDNFQELTADPSIITSSSFKTDRKTRFIIHGFIDKGEESWLANMCKKMFVVESVNC
ICVDWKSGSRTGYTQASQNIRIVGAEVAYFVEVLQSAFGYSPSDVHIIGHSLGAHAAGE
AGRRLNGTAGRITGLDPAEPCFEGTPELVRLDPSDAQFVDVIHTDAAPIIPNMGFGMSQ
TVGHLDFFPNGGKEMPGCQKNILSQIVDIDGIWEGTRDFVACNHLRSYKYYSDSILNPD
GFAGFPCASYNVFTANKCFPCPSEGCPQMGHYADRFPGKTDKVNQIFYLDTGDASNFAR
WRYKVAVTLSGKKVTGHVLVSLFGNKGNSKQYEIFKGTLQPESTHSNEFDSDVEVGDVQ
KVKFVWYNNVINPTLPRVGASKITVERNDGKIFNFCSKETVREDILLTLTPC

FIG. 4

Canine Pancreatic Lipase Peptides

```
[SEQ ID NO:10]  FSDDSPWAGIVERPLKILPW
[SEQ ID NO:11]  VERPLKILPWAPKDVNTRLL
[SEQ ID NO:12]  APKDVNTRLLLYTNENPDNF
[SEQ ID NO:13]  LYTNENPDNFQELTADPSII
[SEQ ID NO:14]  QELTADPSIITSSSFKTDRK
[SEQ ID NO:15]  TSSSFKTDRKTRFIIHGFID
[SEQ ID NO:16]  TRFIIHGFIDKGEESWLANM
[SEQ ID NO:17]  KGEESWLANMCKKMFVVESV
[SEQ ID NO:18]  CKKMFVVESVNCICVDWKSG
[SEQ ID NO:19]  NCICVDWKSGSRTGYTQASQ
[SEQ ID NO:20]  SRTGYTQASQNIRIVGAEVA
[SEQ ID NO:21]  NIRIVGAEVAYFVEVLQSAF
[SEQ ID NO:22]  YFVEVLQSAFGYSPSDVHII
[SEQ ID NO:23]  GYSPSDVHIIGHSLGAHAAG
[SEQ ID NO:24]  GHSLGAHAAGEAGRRLNGTA
[SEQ ID NO:25]  EAGRRLNGTAGRITGLDPAE
[SEQ ID NO:26]  GRITGLDPAEPCFEGTPELV
[SEQ ID NO:27]  PCFEGTPELVRLDPSDAQFV
[SEQ ID NO:28]  RLDPSDAQFVDVIHTDAAPI
[SEQ ID NO:29]  DVIHTDAAPIIPNMGFGMSQ
[SEQ ID NO:30]  IPNMGFGMSQTVGHLDFFPN
[SEQ ID NO:31]  TVGHLDFFPNGGKEMPGCQK
[SEQ ID NO:32]  GGKEMPGCQKNILSQIVDID
[SEQ ID NO:33]  NILSQIVDIDGIWEGTRDFV
[SEQ ID NO:34]  GIWEGTRDFVACNHLRSYKY
[SEQ ID NO:35]  ACNHLRSYKYYSDSILNPDG
[SEQ ID NO:36]  YSDSILNPDGFAGFPCASYN
[SEQ ID NO:37]  FAGFPCASYNVFTANKCFPC
[SEQ ID NO:38]  VFTANKCFPCPSEGCPQMGH
[SEQ ID NO:39]  PSEGCPQMGHYADRFPGKTD
[SEQ ID NO:40]  YADRFPGKTDKVNQIFYLDT
[SEQ ID NO:41]  KVNQIFYLDTGDASNFARWR
[SEQ ID NO:42]  GDASNFARWRYKVAVTLSGK
[SEQ ID NO:43]  YKVAVTLSGKKVTGHVLVSL
[SEQ ID NO:44]  KVTGHVLVSLFGNKGNSKQY
[SEQ ID NO:45]  FGNKGNSKQYEIFKGTLQPE
[SEQ ID NO:46]  EIFKGTLQPESTHSNEFDSD
[SEQ ID NO:47]  STHSNEFDSDVEVGDVQKVK
[SEQ ID NO:48]  VEVGDVQKVKFVWYNNVINP
[SEQ ID NO:49]  FVWYNNVINPTLPRVGASKI
[SEQ ID NO:50]  TLPRVGASKITVERNDGKIF
[SEQ ID NO:51]  TVERNDGKIFNFCSKETVRE
[SEQ ID NO:52]  NFCSKETVREDILLTLTPC
```

Purification and characterization of recombinant canine pancreatic lipase (cPLP1)

FIG. 6
Antibody titers to recombinant canine pancreatic lipase protein (cPLP1) from immunized animals
A.
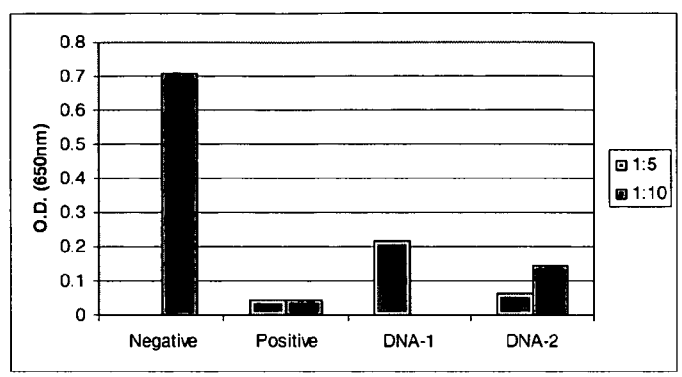
B.
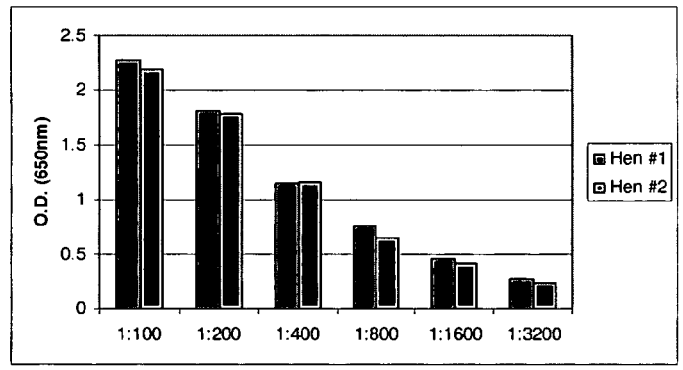

FIG. 7

Reactivity of monoclonal antibodies 7E11 and 4G11 to cPL in canine serum.

| | Lipase (Vitros) | cPLI (O.D.) | | |
|---|---|---|---|---|
| | | 1:2 | 1:10* | |
| Dog 1 | 1276 | 0.203 | 0.111 | 7E11 |
| | | 1.431 | 0.612 | 4G11 |
| Dog 2 | 2085 | 0.965 | 0.235 | 7E11 |
| | | 2.195 | 1.51 | 4G11 |

FIG. 8

Monoclonal antibody 4G11 inhibits the enzymatic activity of cPLP1.

| Sample | Lipase (U/L) |
|---|---|
| cPLP1 1:10 + PBS | 736 |
| cPLP1 1:10 + 7E11 | 717 |
| cPLP1 1:10 + 4G11 | 346 |

FIG. 9

Monoclonal antibodies 4G11 and 7E11 do not compete with each other for binding to cPLP1.

| | O.D. (650) | |
|---|---|---|
| mAb captured | rcPL + BSA | rcPL + mAb |
| 7E11 | 0.541 | 1.059 |
| 4G11 | 0.689 | 0.603 |

FIG. 10

Monoclonal antibody 7E11 competes with an anti-human pancreatic lipase antibody for binding to cPLP1.

|      |        | O.D. (650nm) |       |       |       |
|------|--------|--------------|-------|-------|-------|
|      | rcPL   | No comp      | 1:2   | 1:5   | 1:10  |
| 7E11 | 1:500  | 1.56         | 0.336 | 0.628 | 0.899 |
|      | 1:1000 | 0.885        | 0.160 | 0.322 | 0.445 |
| 4G11 | 1:500  | 1.48         | 1.42  | 1.37  | 1.51  |
|      | 1:1000 | 0.897        | 0.776 | 0.778 | 0.866 |

METHODS TO DETERMINE THE PRESENCE OR AMOUNT OF CANINE PANCREATIC LIPASE WITH ANTIBODIES

CROSS-REFERENCE TO RELATED APPLICATION

This application claims the benefit of U.S. provisional patent application Ser. No. 60/562,836 filed Apr. 16, 2004 and U.S. provisional patent application Ser. No. 60/564,333 filed Apr. 22, 2004.

BACKGROUND OF THE INVENTION

1. Field of the Invention

The invention is related to the detection of pancreatic lipase. More specifically, the invention relates to pancreatic lipase polypeptides, polynucleotides encoding the polypeptides; antibodies specific for the polypeptides, and method of using the polypeptides and antibodies to detect pancreatic lipase in biological samples.

2. Description of Related Art

Complete citations to the references described herein by author and date are provided in the Bibliography section at the end of the specification.

Lipases are water-soluble enzymes that hydrolyze water-insoluble substrates into more polar lipolysis products (Petersen and Drablos 1994). A plethora of lipases have been identified in microorganisms, plants, and animals (Lin et al., 1986; Jaeger et al., 1994; Petersen and Drablos, 1994; Mukherjee and Hills, 1994; Lawson et al., 1994). Lipases share a common triad of amino acids (serine, aspartic or glutamic acid, and histidine) in the active site, which is also shared with serine proteases (Svendsen, 1994). Another common feature of almost all lipases are glycosylation site motifs (Antonian, 1988). Many lipases have been shown to be related phylogenetically. The pancreatic lipase gene family is a large gene family with 9 subfamilies (Petersen and Drablos, 1994; Carriere et al., 1997; Carriere et al., 1998; Hirata et al., 1999). In addition there are other groups of phylogenetically related lipases, and yet other lipases that do not belong to a defined gene family (Anderson and Sando, 1991).

The main function of lipases is the hydrolysis of lipids. A lipase is needed whenever an apolar lipid needs to cross a biological membrane. Triglycerides are prime examples of apolar lipids. Thus lipase is needed in order for triglycerides to be absorbed from the intestinal tract. There are two digestive lipases in most vertebrate species, i.e., a preduodenal lipase and classical pancreatic lipase (Carriere et al., 1994). Preduodenal lipase has been shown to originate from a single tissue in all species examined to date (Moreau et al., 1988). A pharyngeal lipase was identified in cows and sheep, a lingual lipase in rats and mice, and a gastric lipase in human beings, monkeys, horses, pigs, guinea pigs, cats, and dogs (Moreau et al., 1988). No preduodenal lipase could be identified in chickens (Moreau et al., 1988). In human beings and dogs it has been shown that gastric lipase contributes significantly to the digestion of dietary triglycerides (Carriere et al., 1993a; Carriere et al., 1993b). However, pancreatic lipase (also called classical pancreatic lipase) is the most important enzyme in the digestion of dietary triglycerides (Carriere et al., 1991; Carriere et al., 1993a).

It has recently been shown by immunolocalization that pancreatic lipase is only in pancreatic acinar cells in clinically healthy dogs, suggesting that classical pancreatic lipase may be an ideal marker for function and pathology of the exocrine pancreas (Steiner et al., 2002). This hypothesis has been confirmed in clinical studies that have shown that the measurement of pancreatic lipase immunoreactivity in serum is a specific marker for exocrine pancreatic function and also highly sensitive for pancreatitis in the dog (Steiner et al., 2001a; Steiner et al., 2001b; Steiner et al., 2001c).

Pancreatic lipase has an approximate molecular weight of 50 kilodaltons. The purification of classical pancreatic lipase has been reported in many species (Vandermeers and Chroistophe, 1968; Rathelot et al., 1981; Bosc-Bieme et al., 1984; Gieseg et al., 1992; Mejdoub et al., 1994; Steiner and Williams, 2003).

Clinical symptoms of pancreatitis are non-specific and the disease can be difficult to diagnose. Pancreatitis is associated with an increased amount of digestive enzymes and zymogens leaking into the blood stream. One of these enzymes is pancreatic lipase. A number of assays have been developed to detect the presence of lipase in serum by use of catalytic assays. However, these assays lack both sensitivity and specificity for pancreatitis in both human beings and dogs. Accordingly, what is needed is a simple and rapid method and device for sensitively and specifically detecting pancreatic lipase.

SUMMARY OF THE INVENTION

In one aspect, the invention is directed to an isolated nucleic acid molecule having a nucleotide sequence encoding canine pancreatic lipase polypeptides, allelic variants or fragments thereof. The invention includes vectors and host cells containing the sequences, and methods for expressing the polypeptides.

The invention is also directed to monoclonal antibodies that specifically bind to the canine pancreatic lipase polypeptides. The invention further provides for a cell line secreting the monoclonal antibodies.

Another aspect of the invention is directed to methods for determining the presence or amount of canine pancreatic lipase in a biological sample. The method includes using the monoclonal antibodies to specifically bind to canine pancreatic lipase polypeptides in the sample. The method includes using standards of recombinant canine pancreatic lipase.

Further aspects of the invention are directed to devices and kits for performing methods for detecting canine pancreatic lipase in biological samples.

BRIEF DESCRIPTION OF THE FIGURES

FIG. 1 depicts the primer design for the identification and amplification of canine pancreatic lipase. Shown are a series of degenerate primers (1, 2, 3, 5) for 3'RACE (UPM—universal primer mix, Clontech) and nested PCR, as well as the primers used for 5'RACE (4, 6). The region of the previously published N-terminal amino acid sequence is shown.

FIG. 2 shows the 1.429 Kb canine pancreatic lipase gene, designated cPL1 (SEQ ID NO: 2)

FIG. 3 shows the translated canine pancreatic lipase protein, designated cPLP1 (SEQ ID NO. 3). The amino acid sequence was deduced from cDNA sequence analysis.

FIG. 4 shows a number of canine pancreatic lipase peptides [SEQ ID. NOs:10-52] which is generally a series of 20-mer peptides spanning SEQ ID NO. 3 in 10 amino acid sequence overlap.

FIG. 6 depicts the antibody titers to cPLP1 in either DNA immunized mice (A) using a standard competition ELISA with the immune sera or in chickens (B) using the expressed recombinant protein as an immunogen.

FIG. 7 demonstrates the ability of the two monoclonal antibodies, 4G11 and 7E11, to react with canine pancreatic lipase in canine serum.

FIG. 8 depicts the ability of monoclonal antibody 4G11 to inhibit the enzymatic activity of cPLP1.

FIG. 9 contains the ELISA data demonstrating that monoclonal antibodies 4G11 and 7E11 do not compete with each other for binding to cPLP1.

FIG. 10 demonstrates the ability of monoclonal antibody 7E11 to compete with an anti-human pancreatic lipase antibody for binding to cPLP1.

DETAILED DESCRIPTION

Figure 5:
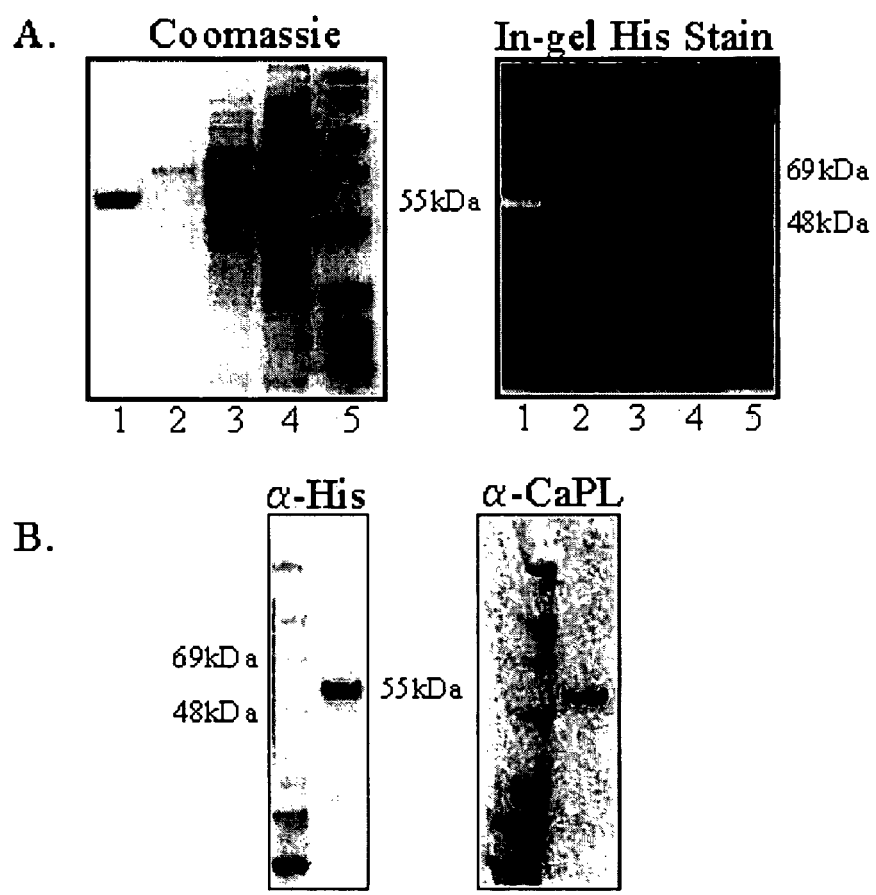
FIG. 5 shows the purified, recombinant canine pancreatic lipase containing a 6× His tag. The protein can be identified in its purified form at approximately 55 kDa on either a Coomassie stained or His-stained gel (A) or on Western blot using an anti-His monoclonal antibody or the 7E11 monoclonal antibody (B).

As used herein, the singular forms "a," "an", and "the" include plural referents unless the context clearly dictates otherwise.

The N-terminal amino acid sequence from purified canine pancreatic lipase has been reported (Steiner and Williams, Biochimie 2002):

KEVCFPRLGCFSDDSPWAGIVERPL [SEQ ID NO:1]

Based on this published amino acid sequence and on sequence similarities among pancreatic lipases of other species, a series of degenerate primers were designed and used for 3'RACE (Rapid Amplification of cDNA Ends) and nested PCR (FIG. 1) from which the complete 3' end of the gene was obtained. Similarly, 5'RACE was used to obtain the 5' end of the gene. The complete gene sequence (cDNA) and translated amino acid sequence is shown in FIGS. 2 and 3.

Accordingly, in one aspect the invention is directed to canine cDNA molecules (e.g. designated herein cPL1, SEQ ID NO. 2), which encode canine lipase proteins such as canine pancreatic lipase protein (e.g. designated herein as cPLP1, (SEQ ID NO. 3). cPLP1 protein, fragments thereof, derivatives thereof, and variants thereof are collectively referred to herein as polypeptides of the invention or proteins of the invention.

Accordingly, in one aspect, the invention is directed to isolated nucleic acid molecules encoding polypeptides of the invention or biologically active portions thereof. The present invention provides nucleic acid sequences that encode protein molecules that have been identified as being members of the lipase family of proteins and are related to the pancreatic lipase subfamily (protein sequences are provided in FIG. 3, transcript/cDNA sequences are provided in FIG. 2). The peptide sequences provided in FIG. 3, as well as the obvious variants described herein, particularly allelic variants as identified herein and using the information in FIG. 3, will be referred herein as the lipase peptides of the present invention, lipase peptides, or peptides/proteins of the present invention.

The present invention provides isolated peptide and protein molecules that consist of, consist essentially of, or comprise the amino acid sequences of the lipase peptides disclosed in the FIG. 3, (encoded by the nucleic acid molecule shown in FIG. 2,), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the lipase peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated lipase peptide can be purified from cells that naturally express it, purified from cells that have been altered to express it (recombinant), or synthesized using known protein synthesis methods. For example, a nucleic acid molecule encoding the lipase peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 3 (SEQ ID NO:3), for example, proteins encoded by the transcript/cDNA nucleic acid sequences shown in FIG. 2 (SEQ ID NO:2). The amino acid sequence of such a protein is provided in FIG. 3. A protein consists of an amino acid sequence when the amino acid sequence is the final amino acid sequence of the protein.

The present invention further provides proteins that consist essentially of the amino acid sequences provided in FIG. 3 (SEQ ID NO:3), for example, proteins encoded by the transcript/cDNA nucleic acid sequences shown in FIG. 2 (SEQ ID NO:2). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 3 (SEQ ID NO:3), for example, proteins encoded by the transcript/cDNA nucleic acid sequences shown in FIG. 2 (SEQ ID NO:2). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence)

that are naturally associated with it or heterologous amino acid residues/peptide sequences. Such a protein can have a few additional amino acid residues or can comprise several hundred or more additional amino acids. The preferred classes of proteins that are comprised of the lipase peptides of the present invention are the naturally occurring mature proteins. A brief description of how various types of these proteins can be made/isolated is provided below.

The lipase peptides of the present invention can be attached to heterologous sequences to form chimeric or fusion proteins. Such chimeric and fusion proteins comprise a lipase peptide operatively linked to a heterologous protein having an amino acid sequence not substantially homologous to the lipase peptide. "Operatively linked" indicates that the lipase peptide and the heterologous protein are fused in-frame. The heterologous protein can be fused to the N-terminus or C-terminus of the lipase peptide.

In some uses, the fusion protein does not affect the activity of the lipase peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant lipase peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., Current Protocols in Molecular Biology, 1992). Moreover, many expression vectors are commercially available that already encode a fusion moiety (e.g., a GST protein). A lipase peptide-encoding nucleic acid can be cloned into such an expression vector such that the fusion moiety is linked in-frame to the lipase peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the lipase peptides of the present invention. The degree of homology/identity present will be based primarily on whether the peptide is a functional variant or non-functional variant, and the amount of divergence present in the paralog family.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). In a preferred embodiment, the percent identity between two amino acid sequences is determined using the Needleman and Wunsch (J. Mol. Biol. (48): 444-453 (1970)) algorithm which has been incorporated into the GAP program in the GCG software package (available at World Wide Web gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG soRware package (Devereux, J., et al, Nucleic Acids Res. 12(1):387 (1984)) (available at World Wide Web gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11-17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (J. Mol. Biol. 215: 403-10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (Nucleic Acids Res. 25(17):3389-3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the lipase peptides of the present invention as well as being encoded by the same genetic locus as the lipase peptide provided herein.

Allelic variants of a lipase peptide can readily be identified as being a canine protein having a high degree (significant) of sequence homology/identity to at least a portion of the lipase peptide as well as being encoded by the same genetic locus as the lipase peptide provided herein. As used herein, two proteins (or a region of the proteins) have significant homology when the amino acid sequences are typically at least about 70-80%, 80-90%, and more typically at least about 90-95% or more homologous. A significantly homologous amino acid sequence, according to the present invention, will be encoded by a nucleic acid sequence that will hybridize to a lipase peptide encoding nucleic acid molecule under stringent conditions as more fully described below.

Paralogs of a lipase peptide can readily be identified as having some degree of significant sequence homology/identity to at least a portion of the lipase peptide, as being encoded by a gene from canines, and as having similar activity or function. Two proteins will typically be considered paralogs when the amino acid sequences are typically at least about 60%, or greater, and more typically at least about 70% or greater homology through a given region or domain. Such paralogs will be encoded by a nucleic acid sequence that will hybridize to a lipase peptide encoding nucleic acid molecule under moderate to stringent conditions as more fully described below.

Non-naturally occurring variants of the lipase peptides of the present invention can readily be generated using recombinant techniques. Such variants include, but are not limited to deletions, additions and substitutions in the amino acid sequence of the lipase peptide. For example, one class of substitutions are conserved amino acid substitution. Such substitutions are those that substitute a given amino acid in a lipase peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., Science 247:1306-1310 (1990).

Variant lipase peptides can be fully functional or can lack function in one or more activities, e.g. ability to bind substrate, ability to hydrolyze substrate, etc. Fully functional variants typically contain only conservative variation or variation in non-critical residues or in non-critical regions. Functional variants can also contain substitution of similar amino acids that result in no change or an insignificant change in function. Alternatively, such substitutions may positively or negatively affect function to some degree.

Amino acids that are essential for function can be identified by methods known in the art, such as site-directed mutagenesis or alanine-scanning mutagenesis (Cunningham et al., Science 244:1081-1085 (1989)), particularly using the results provided in FIG. 2. The latter procedure introduces single alanine mutations at every residue in the molecule. The resulting mutant molecules are then tested for biological activity such as lipase activity or in assays such as an in vitro proliferative activity. Sites that are critical for binding partner/substrate binding can also be determined by structural analysis such as crystallization, nuclear magnetic resonance or photoaffinity labeling (Smith et al., J. Mol. Biol. 224:899-904 (1992); de Vos et al. Science 255:306-312 (1992)).

The present invention further provides fragments of the lipase peptides, in addition to proteins and peptides that comprise and consist of such fragments. In one aspect, the invention provides for the residues identified in FIG. 4. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a lipase peptide. Such fragments can be chosen based on the ability to retain one or more of the biological activities of the lipase peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the lipase peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis).

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in lipase peptides are described in basic texts, detailed monographs, and the research literature, and they are well known to those of skill in the art (some of these features are identified in FIG. 3).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as Proteins—Structure and Molecular Properties, 2nd Ed., T. E. Creighton, W. H. Freeman and Company, New York (1993). Many detailed reviews are available on this subject, such as by Wold, F., Posttranslational Covalent Modification of Proteins, B. C. Johnson, Ed., Academic Press, New York 1-12 (1983); Seifter et al. (Meth. Enzymol. 182: 626-646 (1990)) and Rattan et al. (Ann. N.Y. Acad. Sci. 663:48-62 (1992)).

Accordingly, the lipase peptides of the present invention also encompass derivatives or analogs in which a substituted amino acid residue is not one encoded by the genetic code, in which a substituent group is included, in which the mature lipase peptide is fused with another compound, such as a compound to increase the half-life of the lipase peptide (for example, polyethylene glycol), or in which the additional amino acids are fused to the mature lipase peptide, such as a leader or secretory sequence or a sequence for purification of the mature lipase peptide or a pro-protein sequence.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, and domain of sequence homology or divergence amongst the family, such as those that can readily be identified using protein alignment methods and as presented in the Figures.

Antibodies are preferably prepared from regions or discrete fragments of the lipase proteins. Antibodies can be prepared from any region of the peptide as described herein. However, preferred regions will include those involved in function/activity and/or lipase/binding partner interaction.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness.

In one aspect, the antibodies of the invention are monoclonal antibodies produced by a mouse myeloma cell line. This cell line can be made by fusing a mouse myeloma cell line with the spleen cells from mice that have been injected with the complete canine pancreatic lipase protein, or antigenic portion thereof. As more completely described in the Examples below, two such cell lines have been deposited with the American Type Culture Collection (ATCC), 10801 University Boulevard, Manassas, Va. 20110-2209 on Mar. 31, 2005. These cell lines have been assigned Patent Deposit Numbers PTA-6652 and PTA-6653. The deposits will be maintained under the terms of the Budapest Treaty on the International Recognition of the Deposit of Microorganisms. The deposits are provided as a convenience to those of skill in the art and are not an admission that the deposit is required under 35 U.S.C. § 112. The antibodies secreted from the cell lines have been designated 4G11 and 7E11.

Both antibodies bind to either the purified, native canine pancreatic lipase or the recombinant cPLP1. The antibodies do not compete for the same epitope on cPLP1 and can be used in a sandwich ELISA. Both antibodies bind native canine pancreatic lipase in canine serum. Antibody 4G11 partially inhibits the enzymatic activity of cPLP1, whereas 7E11 does not. Antibody 7E11 detects cPLP1 protein on Western blots, whereas 4G11 does not. 7E11 competes with an anti-human pancreatic lipase antibody for binding to cPLP1, whereas 4G11 does not. Antibody 4G11 appears to have a greater affinity for the cPLP1 than does 7E11 based on the OD's obtained from a sandwich ELISA.

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells, tissues or fluids to determine the pattern of expression of the protein among various tissues in an organism and over the course of normal development. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. If a disorder is characterized by a specific mutation in the protein, antibodies specific for this mutant protein can be used to assay for the presence of the specific mutant protein.

Polynucleotides

The invention provides isolated polynucleotides encoding the canine pancreatic lipase. The term "lipase polynucleotide" or "lipase nucleic acid" refers to the sequence shown in SEQ ID NO:2. The term "lipase polynucleotide" or "lipase nucleic acid" further includes variants and fragments of the lipase polynucleotide.

An "isolated" lipase nucleic acid is one that is separated from other nucleic acid present in the natural source of the lipase nucleic acid. Preferably, an "isolated" nucleic acid is free of sequences which naturally flank the lipase nucleic acid (i.e., sequences located at the 5' and 3' ends of the nucleic acid) in the genomic DNA of the organism from which the nucleic acid is derived. However, there can be some flanking nucleotide sequences, for example up to about 5 KB. The important point is that the lipase nucleic acid is isolated from flanking sequences such that it can be subjected to the specific manipulations described herein, such as recombinant expression, preparation of probes and primers, and other uses specific to the lipase nucleic acid sequences.

Moreover, an "isolated" nucleic acid molecule, such as a cDNA or RNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

In some instances, the isolated material will form part of a composition (for example, a crude extract containing other substances), buffer system or reagent mix. In other circumstances, the material may be purified to essential homogeneity, for example as determined by PAGE or column chromatography such as HPLC. Preferably, an isolated nucleic acid comprises at least about 50, 80 or 90% (on a molar basis) of all macromolecular species present.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

In some instances, the isolated material will form part of a composition (or example, a crude extract containing other substances), buffer system or reagent mix. In other circumstances, the material may be purified to essential homogeneity, for example as determined by PAGE or column chromatography such as HPLC. Preferably, an isolated nucleic acid comprises at least about 50, 80 or 90% (on a molar basis) of all macromolecular species present.

The lipase polynucleotides can encode the mature protein plus additional amino or carboxyterminal amino acids, or amino acids interior to the mature polypeptide (when the mature form has more than one polypeptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

The lipase polynucleotides include, but are not limited to, the sequence encoding the mature polypeptide alone, the sequence encoding the mature polypeptide and additional coding sequences, such as a leader or secretory sequence (e.g., a pre-pro or pro-protein sequence), the sequence encoding the mature polypeptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the polynucleotide may be fused to a marker sequence encoding, for example, a peptide that facilitates purification.

Lipase polynucleotides can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (opposite or anti-sense strand).

Lipase nucleic acid can comprise the nucleotide sequence shown in SEQ ID NO:2, corresponding to canine cDNA. In one embodiment, the lipase nucleic acid comprises only the coding region.

The invention further provides variant lipase polynucleotides, and fragments thereof, that differ from the nucleotide sequence shown in SEQ ID NO:2 due to degeneracy of the genetic code and thus encode the same protein as that encoded by the nucleotide sequence shown in SEQ ID NO:2.

The invention also provides lipase nucleic acid molecules encoding the variant polypeptides described herein. Such polynucleotides may be naturally occurring, such as allelic variants (same locus), homologs (different locus) or may be constructed by recombinant DNA methods or by chemical synthesis. Such non-naturally occurring variants may be made by mutagenesis techniques, including those applied to polynucleotides, cells, or organisms. Accordingly, as discussed above, the variants can contain nucleotide substitutions, deletions, inversions and insertions.

Typically, variants have a substantial identity with a nucleic acid molecule of SEQ ID NO:2 and the complements thereof. Variation can occur in either or both the coding and non-coding regions. The variations can produce both conservative and non-conservative amino acid substitutions. Homologs, and allelic variants can be identified using methods well known in the art. These variants comprise a nucleotide sequence encoding a lipase that is at least about 60-65%, 65-70%, typically at least about 70-75%, more typically at least about 80-85%, and most typically at least about 90-95% or more homologous to the nucleotide sequence shown in SEQ ID NO:2. Such nucleic acid molecules can readily be identified as being able to hybridize under stringent conditions, to the nucleotide sequence shown in SEQ ID NO:2 or a fragment of the sequence. It is understood that stringent hybridization does not indicate substantial homology where it is due to general homology, such as poly A sequences, or sequences common to all or most proteins or all lipase enzymes. Moreover, it is understood that variants do not include any of the nucleic acid sequences that may have been disclosed prior to the invention.

As used herein, the term "hybridizes under stringent conditions" is intended to describe conditions for hybridization and washing under which nucleotide sequences encoding a polypeptide at least about 60-65% homologous to each other typically remain hybridized to each other. The conditions can be such that sequences at least about 65%, at least about 70%, at least about 75%, at least about 80%, at least about 90%, at least about 95% or more identical to each other remain hybridized to one another. Such stringent conditions are known to those skilled in the art and can be found in Current Protocols in Molecular Biology, John Wiley & Sons, N.Y. (1989), 6.3.1-6.3.6, incorporated by reference. One example of stringent hybridization conditions are hybridization in 6× sodium chloride/sodium citrate (SSC) at about 45° C., followed by one or more washes in 0.2×SSC, 0.1% SDS at 50-65° C. In another non-limiting example, nucleic acid molecules are allowed to hybridize in 6× sodium chloride/sodium citrate (SSC) at about 45° C., followed by one or more low stringency washes in 0.2×SSC/0.1% SDS at room temperature, or by one or more moderate stringency washes in 0.2× SSC/0.1% SDS at 42° C., or washed in 0.2×SSC/0.1% SDS at 65° C. for high stringency. In one embodiment, an isolated nucleic acid molecule that hybridizes under stringent conditions to the sequence of SEQ ID NO:2 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

As understood by those of ordinary skill, the exact conditions can be determined empirically and depend on ionic strength, temperature and the concentration of destabilizing agents such as formamide or denaturing agents such as SDS. Other factors considered in determining the desired hybridization conditions include the length of the nucleic acid sequences, base composition, percent mismatch between the hybridizing sequences and the frequency of occurrence of subsets of the sequences within other non-identical sequences. Thus, equivalent conditions can be determined by varying one or more of these parameters while maintaining a similar degree of identity or similarity between the two nucleic acid molecules.

The present invention also provides isolated nucleic acids that contain a single or double stranded fragment or portion that hybridizes under stringent conditions to the nucleotide sequence of SEQ ID NO:2 or the complement of SEQ ID NO:2. In one embodiment, the nucleic acid consists of a portion of the nucleotide sequence of SEQ ID NO:2 or the complement of SEQ ID NO:2.

It is understood that isolated fragments include any contiguous sequence not disclosed prior to the invention as well as sequences that are substantially the same and which are not disclosed. Accordingly, if a fragment is disclosed prior to the present invention, that fragment is not intended to be encompassed by the invention. When a sequence is not disclosed prior to the present invention, an isolated nucleic acid fragment is at least about 6, preferably at least about 10, 13, 18, 20, 23 or 25 nucleotides, and can be 30, 40, 50, 100, 200, 500 or more nucleotides in length. Longer fragments, for example, 30 or more nucleotides in length, which encode antigenic proteins or polypeptides described herein are useful.

Furthermore, the invention provides polynucleotides that comprise a fragment of the full-length lipase polynucleotides. The fragment can be single or double-stranded and can comprise DNA or RNA. The fragment can be derived from either the coding or the non-coding sequence.

In another embodiment an isolated lipase nucleic acid encodes the entire coding region. Other fragments include nucleotide sequences encoding the amino acid fragments shown in FIG. 4.

Thus, lipase nucleic acid fragments further include sequences corresponding to the domains described herein, subregions also described, and specific functional sites. Lipase nucleic acid fragments also include combinations of the domains, segments, and other functional sites described above. A person of ordinary skill in the art would be aware of the many permutations that are possible.

Where the location of the domains or sites have been predicted by computer analysis, one of ordinary sill would appreciate that the amino acid residues constituting these domains can vary depending on the criteria used to define the domains. However, it is understood that a lipase fragment includes any nucleic acid sequence that does not include the entire gene. The invention also provides lipase nucleic acid fragments that encode epitope bearing regions of the lipase proteins described herein. Nucleic acid fragments, according to the present invention, are not to be construed as encompassing those fragments that may have been disclosed prior to the invention.

The nucleic acid fragments of the invention provide probes or primers in assays such as those described below. "Probes" are oligonucleotides that hybridize in a base-specific manner to a complementary strand of nucleic acid. Such probes include polypeptide nucleic acids, as described in Nielsen et al. (1991) Science 254:1497-1500. Typically, a probe comprises a region of nucleotide sequence that hybridizes under highly stringent conditions to at least about 15, typically about 20-25, and more typically about 40, 50 or 75 consecutive nucleotides of the nucleic acid sequence shown in SEQ ID NO:2 and the complements thereof. More typically, the probe further comprises a label, e.g., radioisotope, fluorescent compound, enzyme, or enzyme co-factor.

As used herein, the term "primer" refers to a single-stranded oligonucleotide which acts as a point of initiation of template-directed DNA synthesis using well-known methods (e.g., PCR, LCR) including, but not limited to those described herein. The appropriate length of the primer depends on the particular use, but typically ranges from about 15 to 30 nucleotides. The term "primer site" refers to the area of the target DNA to which a primer hybridizes. The term "primer pair" refers to a set of primers including a 5' (upstream) primer that hybridizes with the 5' end of the nucleic acid sequence to be amplified and a 3' (downstream) primer that hybridizes with the complement of the sequence to be amplified.

Where the polynucleotides are used to assess lipase properties or functions, such as in the assays described herein, all or less than all of the entire cDNA can be useful. Assays specifically directed to lipase functions, such as assessing agonist or antagonist activity, encompass the use of known fragments. Further, diagnostic methods for assessing lipase function can also be practiced with any fragment, including those fragments that may have been known prior to the invention. Similarly, in methods involving treatment of lipase dysfunction, all fragments are encompassed including those, which may have been known in the art.

The lipase polynucleotides are useful as a hybridization probe for cDNA and genomic DNA to isolate a full-length cDNA and genomic clones encoding the polypeptide described in SEQ ID NO:3 and to isolate cDNA and genomic clones that correspond to variants producing the same polypeptide shown in SEQ ID NO:3 or the other variants described herein. Variants can be isolated from the same tissue and organism from which the polypeptide shown in SEQ ID NO:3 were isolated, different tissues from the same organism, or from different organisms. This method is useful for isolating genes and cDNA that are developmentally-controlled and therefore may be expressed in the same tissue or different tissues at different points in the development of an organism.

The probe can correspond to any sequence along the entire length of the gene encoding the lipase. Accordingly, it could be derived from 5' noncoding regions, the coding region, and 3' noncoding regions. The nucleic acid probe can be, for example, the full-length cDNA of SEQ ID NO:2 or a fragment thereof that is sufficient to specifically hybridize under stringent conditions to mRNA or DNA.

The lipase polynucleotides are also useful for constructing recombinant vectors. Such vectors include expression vectors that express a portion of, or all of, the lipase polypeptides. Vectors also include insertion vectors, used to integrate into another polynucleotide sequence, such as into the cellular genome, to alter in situ expression of lipase genes and gene products. For example, an endogenous lipase coding sequence can be replaced via homologous recombination with all or part of the coding region containing one or more specifically introduced mutations. The lipase polynucleotides are also useful for expressing antigenic portions of the lipase proteins. The lipase polynucleotides are also useful for making vectors that express part, or all, of the lipase polypeptides. The lipase polynucleotides are also useful as hybridization probes for determining the level of lipase nucleic acid expression. Accordingly, the probes can be used to detect the presence of, or to determine levels of, lipase nucleic acid in cells, tissues, and in organisms. The nucleic acid whose level is determined can be DNA or RNA. Accordingly, probes corresponding to the polypeptides described herein can be used to assess gene copy number in a given cell, tissue, or organism.

This is particularly relevant in cases in which there has been an amplification of the lipase genes.

Vectors/Host Cells

The invention also provides vectors containing the lipase polynucleotides. The term "vector" refers to a vehicle, preferably a nucleic acid molecule that can transport the lipase polynucleotides. When the vector is a nucleic acid molecule, the lipase polynucleotides are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extrachromosomal element where it replicates and produces additional copies of the lipase polynucleotides. Alternatively, the vector may integrate into the host cell genome and produce additional copies of the lipase polynucleotides when the host cell replicates.

The invention provides vectors for the maintenance (cloning vectors) or vectors for expression (expression vectors) of the lipase polynucleotides. The vectors can function in procaryotic or eukaryotic cells or in both (shuttle vectors).

Expression vectors contain cis-acting regulatory regions that are operably linked in the vector to the lipase polynucleotides such that transcription of the polynucleotides is allowed in a host cell. The polynucleotides can be introduced into the host cell with a separate polynucleotide capable of affecting transcription. Thus, the second polynucleotide may provide a trans-acting factor interacting with the cis-regulatory control region to allow transcription of the lipase polynucleotides from the vector. Alternatively, a trans-acting factor may be supplied by the host cell. Finally, a trans-acting factor can be produced from the vector itself.

It is understood, however, that in some embodiments, transcription and/or translation of the lipase polynucleotides can occur in a cell-free system.

The regulatory sequence to which the polynucleotides described herein can be operably linked include promoters for directing mRNA transcription. These include, but are not limited to, the left promoter from bacteriophage lambda, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al. (1989) Molecular Cloning: A Laboratory Manual 2nd. ed., Cold Spring Harbor Laboratory Press, Cold Spring Harbor, N.Y.).

A variety of expression vectors can be used to express a lipase polynucleotide. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al. (1989) Molecular Cloning: A Laboratory Manual 2nd. ed., Cold Spring Harbor Laboratory Press, Cold Spring Harbor, N.Y.

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The lipase polynucleotides can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate polynucleotide can be introduced into an appropriate host cell for propagation or expression using well-known techniques. Bacterial cells include, but are not limited to, *E. coli, Streptomyces*, and *Salmonella typhimurium*. Eukaryotic cells include, but are not limited to, yeast, insect cells such as *Drosophila*, animal cells such as COS and CHO cells, and plant cells.

As described herein, it may be desirable to express the polypeptide as a fusion protein. Accordingly, the invention provides fusion vectors that allow for the production of the lipase polypeptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired polypeptide can ultimately be separated from the fusion moiety. Proteolytic enzymes include, but are not limited to, factor Xa, thrombin, and enterokinase. Typical fusion expression vectors include pGEX (Smith et al. (1988) Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al. (1988) Gene 69:301-315) and pET 11d (Studier et al. (1990) Gene Expression Technology: Methods in Enzymology 185:60-89).

Recombinant protein expression can be maximized in a host bacteria by providing a genetic background wherein the host cell has an impaired capacity to proteolytically cleave the recombinant protein. (Gottesman, S. (1990) Gene Expression Technology: Methods in Enzymology 185, Academic Press, San Diego, Calif. 119-128). Alternatively, the sequence of the polynucleotide of interest can be altered to provide preferential codon usage for a specific host cell, for example *E. coli*. (Wada et al. (1992) Nucleic Acids Res. 20:2111-2118).

The lipase polynucleotides can also be expressed by expression vectors that are operative in yeast. Examples of vectors for expression in yeast e.g., *S. cerevisiae* include pYepSec1 (Baldari et al. (1987) EMBO J. 6:229-234), pMFa (Kujan et al. (1982) Cell 30:933-943), pJRY88 (Schultz et al. (1987) Gene 54:113-123), and pYES2 (Invitrogen Corporation, San Diego, Calif.).

The lipase polynucleotides can also be expressed in insect cells using, for example, baculovirus expression vectors. Baculovirus vectors available for expression of proteins in cultured insect cells (e.g., Sf9 anc Sf21 cells) include the pAc series (Smith et al. (1983) Mol. Cell Biol. 3:2156-2165) and the pVL series (Lucklow et al. (1989) Virology 170:31-39).

In certain embodiments of the invention, the polynucleotides described herein are expressed in mammalian cells using mammalian expression vectors. Examples of mammalian expression vectors include pCDM8 (Seed, B. (1987) Nature 329:840), pMT2PC (Kauffman et al. (1987) EMBO J. 6:187-195).

The expression vectors listed herein are provided by way of example only of the well-known vectors available to those of ordinary skill in the art that would be useful to express the lipase polynucleotides. The person of ordinary skill in the art would be aware of other vectors suitable for maintenance propagation or expression of the polynucleotides described herein. These are found for example in Sambrook et al. (1989) Molecular Cloning: A Laboratory Manual 2nd, ed., Cold Spring Harbor Laboratory, Cold Spring Harbor Laboratory Press, Cold Spring Harbor, N.Y.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the polynucleotide sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook et al. (Molecular Cloning: A Laboratory Manual, 2d ed., Cold Spring Harbor Laboratory, Cold Spring Harbor Laboratory=Press, Cold Spring Harbor, N.Y.).

Host cells can contain more than one vector. Thus, different nucleotide sequences can be introduced on different vectors of the same cell. Similarly, the lipase polynucleotides can be introduced either alone or with other polynucleotides that are not related to the lipase polynucleotides such as those providing trans-acting factors for expression vectors. When more than one vector is introduced into a cell, the vectors can be introduced independently, co-introduced or joined to the lipase polynucleotide vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the polynucleotides described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the polypeptide is desired, appropriate secretion signals are incorporated into the vector. The signal sequence can be endogenous to the lipase polypeptides or heterologous to these polypeptides.

Where the polypeptide is not secreted into the medium, the protein can be isolated from the host cell by standard disruption procedures, including freeze thaw, sonication, mechanical disruption, use of lysing agents and the like. The polypeptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the polypeptides described herein, the polypeptides can have various glycosylation patterns, depending upon the cell, or maybe non-glycosylated as when produced in bacteria. In addition, the polypeptides may include an initial modified methionine in some cases as a result of a host-mediated process.

It is understood that "host cells" and "recombinant host cells" refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

Exemplary antigenic and enzymatic characteristics of cPLP1 which are exhibited by such polypeptides include lipase activity, ability to bind with molecules with which cPLP1 is able to bind, and ability to induce production of antibody substances which bind specifically with an epitope which occurs at or near the surface of the cPLP1 protein. The polypeptides of the invention, or biologically active portions thereof, can be operably linked with a heterologous amino acid sequence to form fusion proteins. In addition, one or more polypeptides of the invention or biologically active portions thereof can be incorporated into pharmaceutical compositions, which can optionally include pharmaceutically acceptable carriers. Such pharmaceutical compositions can be used to treat or prevent one or more of the disorders identified herein. The invention encompasses antibody substances that specifically bind with a polypeptide of the invention including, for example, cPLP1 protein and fragments thereof. Exemplary antibody substances that are included within the scope of the invention are monoclonal and polyclonal antibodies, antibody fragments, single-chain antibodies, free and cell-surface-bound antibodies, and T cell receptors. These antibody substances can be made, for example, by providing the polypeptide of the invention to an immunocompetent vertebrate and thereafter harvesting blood or serum from the vertebrate. Antibody substances can, alternatively, be generated by screening a library of phage to identify phage particles which display a subunit which binds with cPLP1 or an epitope thereof.

In another aspect, the invention provides methods for detecting activity or expression of a polypeptide of the invention in a biological sample by contacting the biological sample with an agent capable of detecting such activity (e.g., a labeled substrate or another compound that can be detected after being acted upon by an active polypeptide of the invention), with an agent which binds specifically with a polypeptide of the invention (e.g., an antibody substance of the invention), or with an agent for detecting production of an RNA encoding a polypeptide of the invention (e.g., a reverse transcriptase primer complementary to a portion of an mRNA encoding the polypeptide).

Detection of Canine Pancreatic Lipase

In one aspect, the invention is directed to an immunological method for detecting the presence of an amount of canine pancreatic lipase in a biological sample. The invention provides a method, a device and a kit that uses one or more canine lipase monoclonal antibodies. In another aspect, the method includes calibrators and standards comprising one or more canine pancreatic lipase polypeptides.

"Binding specificity" or "specific binding" refers to the substantial recognition of a first molecule for a second molecule, for example a polypeptide and a polyclonal or monoclonal antibody, or an antibody fragment (e.g. a Fv, single chain Fv, Fab', or F(ab')2 fragment) specific for the polypeptide.

A "specific binding pair" is a set of two different molecules, where one molecule has an area on its surface or in a cavity that specifically binds to, and is therefore complementary to, an area on the other molecule. "Specific binding partner" refers to one of these two complementarily binding molecules. "Specific binding pair" may refer to a ligand and a receptor, for example. In another example, the specific binding pair might refer to an immunological pair, for example an antigen and antibody.

"Substantial binding" or "substantially bind" refer to an amount of specific binding or recognizing between molecules in an assay mixture under particular assay conditions. In its broadest aspect, substantial binding relates to the difference between a first molecule's incapability of binding or recognizing a second molecule, and the first molecules capability of binding or recognizing a third molecule, such that the difference is sufficient to allow a meaningful assay to be conducted distinguishing specific binding under a particular set of assay conditions, which includes the relative concentrations of the molecules, and the time and temperature of an incubation. In another aspect, one molecule is substantially incapable of binding or recognizing another molecule in a cross-reactivity sense where the first molecule exhibits a reactivity for a second molecule that is less than 25%, preferably less than 10%, more preferably less than 5% of the reactivity exhibited toward a third molecule under a particular set of assay conditions, which includes the relative concentration and incubation of the molecules. Specific binding can be tested using a number of widely known methods, e.g, an immunohistochemical assay, an enzyme-linked immunosorbent assay (ELISA), a radioimmunoassay (RIA), or a western blot assay.

A "biological sample" refers to a sample from an animal subject including whole blood, serum, plasma, tissue, abdominal fluid (ascites), urine or other sample known or suspected to contain canine pancreatic lipase.

A "label" is any molecule that is bound (via covalent or non-covalent means, alone or encapsulated) to another molecule or solid support and that is chosen for specific characteristics that allow detection of the labeled molecule. Generally, labels are comprised of, but are not limited to, the following types: particulate metal and metal-derivatives, radioisotopes, catalytic or enzyme-based reactants, chromogenic substrates and chromophores, fluorescent and chemiluminescent molecules, and phosphors. The utilization of a label produces a signal that may be detected by means such as detection of electromagnetic radiation or direct visualization, and that can optionally be measured.

The label employed in the current invention could be, but is not limited to: alkaline phosphatase; glucose-6-phosphate dehydrogenase ("G6PDH"); horse radish peroxidase (HRP); chemiluminescers such as isoluminol, fluorescers such as fluorescein and rhodamine compounds; ribozymes; and dyes.

The label can directly produce a signal, and therefore additional components are not required to produce a signal. Alternatively, a label may need additional components, such as substrates or co-enzymes, in order to produce a signal. The suitability and use of such labels useful for producing a signal are discussed in U.S. Pat. No. 6,489,309, and U.S. Pat. No. 5,185,243, which are incorporated by reference herein in their entirety. For example, a label may be conjugated to the specific binding partner in a non-covalent fashion. Alternatively, the label may be conjugated to the specific binding partner covalently. U.S. Pat. No 3,817,837, and U.S. Pat. No. 3,996,345, which are incorporated by reference herein in their entirety, describe in detail example of various ways that a label may be non-covalently or covalently conjugated to the specific binding partner.

Solid phase means a porous or non-porous water insoluble material. Such materials include a support or a surface such as the wall of a reaction vessel. The support can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly(4-methylbutene), polystyrene, polymethacrylate, poly(ethylene terephthalate), nylon, poly(vinyl butyrate), etc.; either used by themselves or in conjunction with other materials; glass available as Bioglass, ceramics, metals, and the like. Natural or synthetic assemblies such as liposomes, phospholipid vesicles, and cells can also be employed.

Binding of sbp members to a support or surface may be accomplished by well-known techniques, commonly available in the literature. See, for example, "Immobilized Enzymes," Ichiro Chibata, Halsted Press, New York (1978) and Cuatrecasas, J. Biol. Chem., 245:3059 (1970). The surface can have any one of a number of shapes, such as strip, rod, particle, including bead, and the like. In one aspect, the polypeptides of the invention include a N-terminal cysteine residue to assist in binding the polypeptides to the solid phase.

The method of the invention can be optimized in many ways and one of skill in the art could simultaneously adjust the sample dilutions, reagent concentrations, incubation temperatures and times used in the method to accomplish detection of canine pancreatic lipase.

To be useful in the detection methods of the present invention, the polypeptides are obtained in a substantially pure form, that is, typically from about 50% w/w or more purity, substantially free of interfering proteins and contaminants. Preferably, the polypeptides are isolated or synthesized in a purity of at least 80% w/w, and more preferably, in at least about 95% w/w purity. Using conventional protein purification techniques, homogeneous polypeptide compositions of at least about 99% w/w purity can be obtained. For example, the proteins may be purified by use of the antibodies described hereinafter using the immunoabsorbant affinity columns described hereinabove.

The method of the invention may be accomplished using immunoassay techniques well known to those of skill in the art, including, but not limited to, using microplates and lateral flow devices. In one embodiment, an antibody specific for canine pancreatic lipase protein is immobilized on a solid support at a distinct location. Following addition of the sample, detection of protein-antibody complexes on the solid support can be by any means known in the art. For example, U.S. Pat. No. 5,726,010, which is incorporated herein by reference in its entirety, describes an example of a lateral flow device, the SNAP® immunoassay device (IDEXX Laboratories), useful in the present invention. In another aspect, the solid support is a well of a microtiter plate.

Immobilization of one or more analyte capture reagents, e.g., antibodies to canine pancreatic lipase, onto a device or solid support is performed so that an analyte capture reagent will not be washed away by the sample, diluent and/or wash procedures. One or more analyte capture reagents can be attached to a surface by physical adsorption (i.e., without the use of chemical linkers) or by chemical binding (i.e., with the use of chemical linkers). Chemical binding can generate stronger attachment of specific binding substances on a surface and provide defined orientation and conformation of the surface-bound molecules.

In another aspect, the invention includes one or more labeled specific binding reagents that can be mixed with a test sample prior to application to a device for of the invention. In this case it is not necessary to have labeled specific binding reagents deposited and dried on a specific binding reagent pad in the device. A labeled specific binding reagent, whether added to a test sample or pre-deposited on the device, can be for example, a labeled canine pancreatic lipase monoclonal antibody.

When the analyte capture reagent and the labeled specific binding reagent are antibodies that specifically bind canine pancreatic lipase, the antibodies may be the same or different. In one aspect, the antibodies are chosen from 4G11 and 7E11 antibodies.

The detection method may include the use of a standard such as a recombinant canine pancreatic lipase polypeptide. The standard can be mixed with the monoclonal antibody or antibodies in the same manner as the sample. The amount of binding between the monoclonal antibody or antibodies and the standard can be compared to the amount of binding of the antibodies to the protein in the sample. Accordingly, because the amount of canine pancreatic lipase in the standard is known, the amount of protein in the sample can be determined.

Any or all of the above embodiments can be provided as a kit. In one particular example, such a kit would include a device complete with specific binding reagents (e.g., a non-immobilized labeled specific binding reagent and an immobilized analyte capture reagent) and wash reagent, as well as detector reagent and positive and negative control reagents, if desired or appropriate. In addition, other additives can be included, such as stabilizers, buffers, and the like. The relative amounts of the various reagents can be varied, to provide for concentrations in solution of the reagents that substantially optimize the sensitivity of the assay. Particularly, the reagents can be provided as dry powders, usually lyophilized, which on dissolution will provide for a reagent solution having the appropriate concentrations for combining with a sample.

The device may also include a liquid reagent that transports unbound material (e.g., unreacted fluid sample and unbound specific binding reagents) away from the reaction zone (solid phase). A liquid reagent can be a wash reagent and serve only to remove unbound material from the reaction zone, or it can include a detector reagent and serve to both remove unbound material and facilitate analyte detection. For example, in the case of a specific binding reagent conjugated to an enzyme, the detector reagent includes a substrate that produces a detectable signal upon reaction with the enzyme-antibody conjugate at the reactive zone. In the case of a labeled specific binding reagent conjugated to a radioactive, fluorescent, or light-absorbing molecule, the detector reagent acts merely as a wash solution facilitating detection of complex formation at the reactive zone by washing away unbound labeled reagent.

Two or more liquid reagents can be present in a device, for example, a device can comprise a liquid reagent that acts as a wash reagent and a liquid reagent that acts as a detector reagent and facilitates analyte detection.

A liquid reagent can further include a limited quantity of an "inhibitor", i.e., a substance that blocks the development of the detectable end product. A limited quantity is an amount of inhibitor sufficient to block end product development until most or all excess, unbound material is transported away from the second region, at which time detectable end product is produced.

In another aspect, the invention is directed to a kit for detecting canine pancreatic lipase. For example the kit can include the device described above, along with the antibodies described herein. One or more of the peptides of the invention can be included as a calibrator and control. Such a kit can be supplied to detect a single protein or epitope or can be configured to detect one of a multitude of epitopes, such as in an antibody detection array. In one aspect, the kit includes a solid phase, such as a microtiter plate or lateral flow device, having an immobilized antibody specific for canine pancreatic lipase, a reagent comprising a second labeled antibody specific for canine pancreatic lipase, and reagents for use in detecting the label. The kit also includes the appropriate packaging and instructions.

Other features and advantages of the invention will be apparent from the following Examples. The following are provided for exemplification purposes only and are not intended to limit the scope of the invention described in broad terms above. All references cited in this disclosure are incorporated herein by reference.

EXAMPLE 1

Cloning and Characterization of the Canine Pancreatic Lipase (cPL1) Gene from Pancreatic Tissue Based on the published N-terminal amino acid sequence of purified canine pancreatic lipase (Steiner and Williams, Biochimie 2002) (SEQ ID NO. 1) and sequence similarities among pancreatic lipases of other species, a series of degenerate primers were designed and used for 3'RACE and nested PCR (FIG. 1). These primers targeted specific regions of the pancreatic lipase amino acid sequence which differentiate it from other members of the pancreatic lipase family, namely the pancreatic lipase related proteins. Total RNA was purified from canine pancreas using TRIZOL® reagent (Invitrogen) and then reverse transcribed to cDNA using a commercially available kit (SMART™ RACE cDNA Amplification Kit, Clontech). The 3'RACE reaction and nested PCR were successful in obtaining a 1.4 kb segment of the canine pancreatic lipase gene that extended through to the appropriate stop codon. To complete the gene sequence, cDNA for 5' RACE was generated and specific primers within the canine gene were designed for the RACE reaction as shown in FIG. 1. This amplification was successful in obtaining the complete 5' end of the gene. The complete gene sequence (cDNA, SEQ ID NO: 2) and translated amino acid sequence (SEQ ID NO: 3) are shown in FIGS. 2 and 3.

EXAMPLE 2

Expression of Canine Pancreatic Lipase

The gene for canine pancreatic lipase was amplified by PCR from canine pancreatic cDNA using a High Fidelity Taq according to the manufacturer's instructions (Roche) and ligated into a baculovirus expression vector (pBlueBac4.5, Invitrogen). The reverse primer for the PCR contained the nucleotide sequence for a 6× His tag immediately following the codon for the final amino acid of the protein. The purified vector was used for co-transfection with transfer DNA into Sf9 insect cells (Invitrogen) using standard calcium phosphate techniques. Standard baculovirus protocols were followed to generate a high titer stocks of the recombinant virus for infection of Sf21 insect cells and protein production (Invitrogen). Sf21 insect cells were grown in approximately 500 ml serum-free EX-CELL™ 420 culture media (JRH Biosciences) to a concentration of 7-8×$10^8$ cells and infected with 10 ml of virus stock, resulting in an MOI between 1.0-2.0. Following four days of culture, activity of the recombinant cPLP1 protein was measured in the culture supernatant using a standard lipase enzymatic assay (VITROS® Chemistry System, Ortho-Clinical Diagnostics).

The recombinant cPLP1 protein was purified from insect cell culture supernatant following either standard protocols reported in the literature (Thirstrup, K. et al. FEBS, 1993), or by means of the 6× His fusion tag metal chelate affinity chromatography (HISTRAP™ HP affinity column, Amersham Biosciences). The purified protein was buffer exchanged into phosphate buffered saline, pH7.2 using a standard desalting column (PD-10, Amersham Biosciences). The purified recombinant cPLP1 protein was shown to have lipase activity using a standard enzymatic assay (Vitros® Chemistry System).

As shown in FIG. 6A, the purified cPLP1 protein was also characterized on SDS-PAGE gels using a Coomassie protein stain and an in-gel His-tag stain (Pierce) (FIG. 6A, lane 1). Pre-purification fractions are shown in lanes 2-4 with the molecular weight markers shown in lane 5. As shown in FIG. 6B, the purified cPLP1 protein could also be identified on Western blots using an anti-His monoclonal antibody (1:200, anti-6His peroxidase, Roche) or the 7E11 monoclonal antibody (1:250, IDEXX Laboratories, Inc.).

EXAMPLE 3

Use of the Canine Pancreatic Lipase DNA and Polypeptide Sequences for Immunization and Antibody Production The gene for canine pancreatic lipase was amplified by PCR (High Fidelity Taq, Roche) from canine pancreatic cDNA and ligated into a mammalian expression vector (pCMV-Tag4a, Stratagene) at the multiple cloning site. This vector may or may not be constructed with a C-terminal tag. The resulting vector was transiently transfected into COS7L cells using LIPOFECTAMINE™ Transfection Reagent (Invitrogen) to confirm expression of the canine pancreatic lipase protein.

Purified vector DNA (MaxiPrep Kit, Qiagen) was used for DNA immunization of mice according to published protocols (Ulmer, J. B. et al. Science, 1993). Antibody titers from each individual mouse were evaluated two weeks after the second immunization. A 96-well microtiter plate (Immulon 2HB, Dynatech) was coated overnight at 4° C. with 10 μg/ml of an anti-human pancreatic lipase antibody (Fitzgerald #M410139a) in phosphate buffered saline (PBS, pH7.4). The plate was then blocked with 3% BSA in 50 mM Tris (pH7.5) for 1 hour and washed 4 times in PBS-T (0.01M PBS with 0.05% Tween-20 (Sigma)). Sera from an unimmunized (negative control), immune (positive control), and two DNA vaccinated mice were pre-incubated with a 1:1000 dilution of the recombinant, purified cPLP1 protein in antibody diluent (50 mM Tris (pH 7.2), 0.05% Tween-20, with both 50% fetal bovine serum and 10% mouse serum) for five minutes prior to adding it to the sandwich ELISA, thus creating a competition format. The plate was incubated at room temperature for 1 hour followed by 4 washes in PBS-T. The captured cPLP1 was detected using a 1:1000 dilution of a rabbit polyclonal antibody (Texas A&M University, College Station, Tex.) and a 1:2500 dilution of HRPO-conjugated goat anti-rabbit antibody (Jackson ImmunoResearch), in antibody diluent each for 1 hour at room temperature. The plate was washed 6 times with PBS-T and developed with a TMB substrate (Moss, Inc.). As shown in FIG. 6A, reduction in signal (O.D.) relative to the negative control indicates an antibody response to the cPLP1 antigen (FIG. 6A).

The purified, recombinant cPLP1 protein was also used as an immunogen for antibody production in chickens. Two hens were immunized according to standard protocols familiar to those skilled in the art. After a series of four injections, antibody titers were measured using a sandwich ELISA with an anti-chicken HRP conjugate (1:2500, Jackson ImmunoResearch) and the recombinant cPLP1, similar to the ELISA described above. As shown in FIG. 6B, both hens developed reasonable titers to cPLP1.

EXAMPLE 4

Use of Purified, Native Canine Pancreatic Lipase for Immunization and Antibody Production Purified, native canine pancreatic lipase (Steiner and Williams, Biochimie. 2002 December; 84(12): 1245-53) was used to immunize Balb/C mice using methods well known to those skilled in the art (see Antibodies, a Laboratory Manual, by Harlow and Lane, Cold Spring Harbor Laboratory Press, 1988, pp 53-135). Two mice were each immunized with ~63 ug of cPL using complete Freund's adjuvant, intraperitoneally (I.P.) on day 0. On day 25, using Freund's incomplete adjuvant, the mice were boosted using the same procedure. On day 50, using Ribi adjuvant, the mice were boosted using the same procedure.

On day 69, tail bleeds were taken and the anti-cPL titer was determined using an anti-cPL ELISA assay as described in Example 5, below.

On day 98 the mice were boosted subcutaneously (S.C.) with 30 ug of native cPL using Ribi adjuvant. On day 114 the mice were boosted using an identical protocol. On day 123, tail bleeds were taken and the anti-cPL titer was determined using an anti-cPL ELISA assay. On day 143 the mice were boosted intramuscularly in the hind leg with 10 ug of native cPL. On day 147 the spleens were harvested and fused with myeloma cell line FO using methods well know to those skilled in the art (see Antibodies, a Laboratory Manual, by Harlow and Lane, Cold Spring Harbor Laboratory Press, 1988, pp 139-238).

EXAMPLE 5

ELISA for Canine Pancreatic Lipase

The method used for the initial screening of mouse tail bleeds is described by Steiner et al. (Can. J. Vet. Res. 67:175-82). Briefly, canine pancreatic lipase was coated on 96 well microtitre plates at a concentration of 0.3 ug/mi for 1 hour at 37° C. Plates were blocked with Super Block (Pierce) for 1 hour and washed with PBS. Mouse sera samples were diluted 1:10 in PBS with 1% BSA and serially diluted across plate. Plates were incubated for 1 hour at 37° C., followed by 4 washes with PBS/0.05% tween20. Goat anti-mouse HRP conjugate (Jackson Immuno Research) diluted 1:3000 was used to detect bound antibodies. Plates were developed with TMB reagent (Pierce).

EXAMPLE 6

Screening and Isolation of CaPL Monoclonal Antibodies

Hybridoma cell lines were grown as described in Example 4, and individual monoclonal antibody producing clones were isolated using the process of limited dilution. A sandwich ELISA was developed to screen for hybridoma's secreting antibodies specific for cPL.

Mouse monoclonal antibodies were captured from cell supernatants on Immulon 2 HB plates coated with donkey anti-mouse antibodies (Jackson Immuno Research) coated at a concentration of 10 ug/ml. Supernatents were incubated on plates for 2 hours at room temperature (or overnight at 4° C.) to allow for capture to occur. Plates were then washed 6 times with PBS/0.1% Tween20 and incubated with canine pancreatic lipase (0.5 ug/ml, 50 ul/well) for 1 hour and washed again. Rabbit Anti-cPL polyclonal antibody (Texas A&M University, College Station, Tex.) diluted 1:1000 in conjugate diluent (50 mM Tris (pH 7.2), 0.05% Tween-20, 50% fetal bovine serum) was added to wells and incubated for 1 hour. Bound antibody was detected using a donkey anti-rabbit: HRP conjugate (Jackson Immuno Research) diluted 1:2500 in conjugate diluent. Plates were washed 8 times before color development with TMB reagent. Color was allowed to develop for 5 minutes.

This method was used to identify monoclonal antibodies that bound specifically to cPL. For example, two murine monoclonal antibodies were isolated using this method, 4G11 and 7E11. These monoclonal antibodies bind to cPL with suitable affinity for the development of a cPL ELISA assay. The cell lines secreting these antibodies have been deposited with the ATCC, Manassas Va. on Mar. 30, 2005. Strain designations are CPL 7E11 clone 2/A5 and CPL 4G11/14D, bearing ATCC Patent Deposit Numbers PTA-6653 and PTA 6652, respectively.

EXAMPLE 7

Characterization of Monoclonal Antibodies.

Both of the identified monoclonal antibodies, 7E11 and 4G11, react with cPL in canine serum. Reactivity was demonstrated by using the ELISA format described in this example and substituting two canine serum samples (1:2 or 1:10 dilution in 3% BSA, 50 mM Tris (pH7.5)) for the cPLP1. Results are shown in FIG. 7.

Both of the identified monoclonal antibodies, 4G11 and 7E11, were evaluated for their ability to interfere with the enzymatic activity of the cPLP1 in a lipase assay (VITROS® Chemistry System, Ortho-Clinical Diagnostics). Hybridoma supernatant from either 4G11 and 7E11 was mixed with filtered insect cell culture supernatant containing the cPLP1 to give a 1:10 dilution. Lipase activity was compared to a PBS control and an irrelevant hybridoma supernatant. Only the addition of hybridoma supernatant from 4G11 produced a reduction in enzymatic activity on the lipase assay (FIG. 8).

The identified monoclonal antibodies, 4G11 and 7E11, do not compete with each other for binding to cPLP1. Using the ELISA protocol described in this example, either 4G11 or 7E11 antibodies were captured on the plate from the hybridoma supernatant. Recombinant cPLP1 (1:250 for 7E11 or 1:1000 for 4G11) was diluted in the antibody diluent (see Example 3) in the presence of either 10 μl 3% BSA, 10 μl hybridoma sup for 4G11, or 10 μl hybridoma sup for 7E11, before being added to the microtiter plate. A reduction in signal (O.D.) was not observed for either monoclonal antibody when the antigen was pre-incubated with the alternate monoclonal (FIG. 9).

Both identified monoclonal antibodies, 4G11 and 7E11, were tested for their ability to compete with a commercially available monoclonal antibody to human pancreateic lipase which we found to react with the cPLP1. An ELISA was performed as described in Example 3 where an anti-human pancreatic lipase antibody (Fitzgerald M410139a) was coated onto microtiter plates. Wells were blocked with Tris-based Superblock (Pierce) +0.1% Tween-20. Following four washes in PBS-T, cPLP1 at a 1:500 or 1:1000 dilution in antibody diluent (Example 3) was pre-incubated for 10 minutes with either a 1:2, 1:5, or 1:10 dilution of 7E11 or 4G11, respectively prior to addition to the wells. Samples were incubated for 1 hour followed by 5 washes in PBS-T. Detection with the polyclonal antibody to cPL was performed as described in Example 6. As shown in FIG. 10, the anti-human pancreatic lipase antibody does bind to cPLP1, and monoclonal antibody 7E11 competes with this antibody for binding of cPLP1, but monoclonal antibody 4G11 does not.

When the reactivity of the purified monoclonal antibodies, 4G11 and 7E11, are compared under equivalent concentrations, antibody 4G11 gives a greater O.D. (650 nm) reading for an equivalent concentration of cPLP1 than does antibody 7E11. For instance, in an ELISA where each antibody is coated on Immulon 2HB plates in PBS at 10 ug/ml overnight at 4° C. and processed with a 1:500 dilution of cPLP1 as described in Example 3, 4G11 gives an O.D. reading of 1.747 vs. 7E11 which gives an O.D. reading of 1.383. Similarly, if the purified monoclonals are captured in an ELISA as described in Example 6, a 1:4000 dilution of cPLP1 gives an O.D. reading for 4G11 of 1.010 vs. a 1:400 dilution of cPLP1 gives an O.D. reading for 7E11 of 1.140. This data suggests that these two monoclonal antibodies have different binding affinities for the cPLP1 antigen.

When compared biochemically, the two monoclonal antibodies, 4G11 and 7E11, have different isoelectric focusing points. The pI for 4G11 is 6.7 and the pI for 7E11 is 6.1.

EXAMPLE 8

Use of Antibodies Reactive to Canine Pancreatic Lipase

Antibodies recognizing the canine pancreatic lipase may be used in quantitative and non-quantitative assays for the detection of pancreatic lipase in canine serum or other biological samples. In one example, the canine pancreatic lipase assay consists of an ELISA using the sandwich format. In this format, monoclonal Anti-cPL (clone 7E11) is coated onto microtiter plate wells (Immulon 4 HBX plates; Thermo Electron Corp.; catalog number S25-343-04) at a concentration of approximately 5 ug/mL. The coating procedure is as follows: 7E11 monoclonal antibody is diluted to 5 ug/mL in 10 mM phosphate buffered saline (PBS), pH 7.4. To each well, 100 uL of this coating solution is loaded and incubated at 4° C. for 8 hours. The coating solution is then aspirated and the plates are washed in triplicate using 0.1M PBS/0.05% Tween 20. The plates are then loaded with 200 uL per well of BSA-based blocking solution; the plates are incubated at 25° C. for 4 hours. The plates are aspirated and washed three times with 0.1M PBS/0.05% Tween 20. Pancreatic lipase contained in the serum sample or calibrator is captured by the solid-phase antibody. Calibrator preparation consists of diluting recombinant cPL antigen into a BSA-based diluent to give calibrators at the ug/L level. Next, HRPO-conjugated monoclonal Anti-cPL (clone 4G11) is added to complete the sandwich. The HRPO-antibody conjugate is prepared using HRPO-SMCC and a disulfide reduced form of the antibody.

Figure 11:
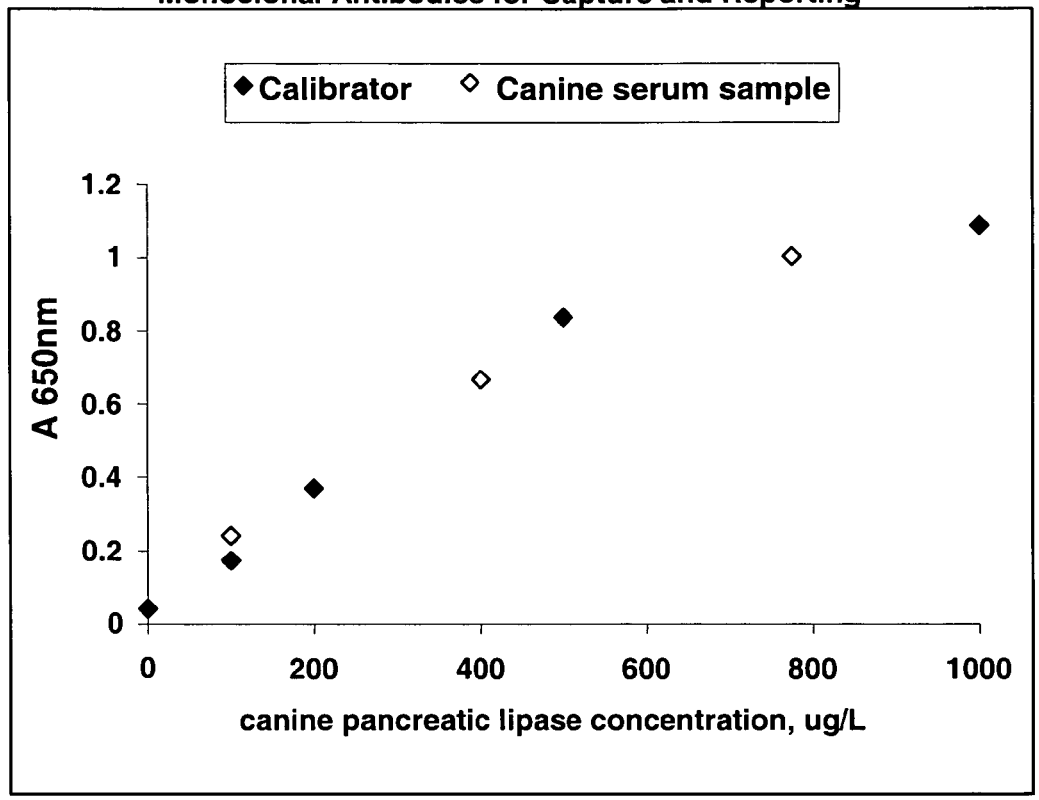
FIG. 11 shows the results of an ELISA sandwich assay for canine pancreatic lipase using monoclonal antibodies 7E11 and 4G11.

For this assay, the pancreatic lipase-containing calibrators and canine patient samples are premixed in individual tubes along with HRPO-Conjugated mAb 4G11. The sample or calibrator to conjugate ratio is 1:3 v/v. A conjugate dilution factor of 1:3000 is used in the assay. No premixture incubation time is required. The calibrator and sample premixtures are then loaded into antibody-coated microtiter plate wells (100 μ), and incubated for one hour at 25° C. At the end of the incubation time, the plate is washed to remove unbound components. TMB substrate is added to the wells, and the plate is incubated for 5 minutes at room temperature. The color reaction is stopped with the addition of 1% SDS solution, and absorbance values are read at 650 nm using a microtiter plate reader. Results using a mAB 7E11 and mAB 4G11 sandwich and premixture protocol are shown in FIG. 11.

Alternatively, a protocol with no premixture may be followed. The calibrator or sample is loaded into the antibody-coated microtiter plate wells, and incubated for one hour at 25° C. The plate is washed to remove unbound materials. The wells are then loaded with the HRPO-conjugated mAB 4G11 and incubated for one hour at 25° C. At the end of the incubation time, the plate is washed to remove unbound components. TMB substrate is added to the wells, and the plate is incubated for 5 minutes at room temperature. The color reaction is stopped with the addition of 1% SDS solution, and absorbance values are read at 650 nm using a microtiter plate reader.

Although various specific embodiments of the invention have been described herein, it is to be understood that the invention is not limited to those precise embodiments and that various changes or modifications can be affected therein by one skilled in the art without departing from the scope and spirit of the invention.

BIBLIOGRAPHY

1. Petersen, S. B., Drablos, F., 1994. A sequence analysis of lipases, esterases, and related proteins. In: Woolley, P., Petersen, S. B. (Eds.), Lipases—their structure, biochemistry, and application, Cambridge University Press, Cambridge, pp. 23-48.
2. Lin, Y. H., Yu, C., Huang, A. H., 1986. Substrate specificities of lipases from corn and other seeds. Arch. Biochem. Biophys. 244, 346-356.
3. Jaeger, K. E., Ransac, S., Dijkstra, B. W., Colson, C., van Heuvel, M., Misset, O., 1994. Bacterial lipases. FEMS Microbiology Reviews 15, 29-63.
4. Mukherjee, K. D., Hills, M. J., 1994. Lipases from plants. In: Woolley, P., Petersen, S. B. (Eds.), Lipases—their structure, biochemistry and application, Cambridge University Press, Cambridge, pp. 49-75.
5. Lawson, D. M., Brzozowski, A. M., Dodson, G. G., Hubbard, R. E., Huge-Jensen, B., Boel, E., Derewenda, Z. S., 1994. Three-dimensional structures of two lipases from filamentous fungi. In: Woolley, P., Petersen, S. B. (Eds.), Lipases—their structure, biochemistry and application, Cambridge University Press, Cambridge, pp. 77-94.
6. Svendsen, A., 1994. Sequence comparisons within the lipase family. In: Woolley, P., Petersen, S. B. (Eds.), Lipases—their structure, biochemistry, and application, Cambridge University Press, Cambridge, pp. 1-21.
7. Antonian, E., 1988. Recent advances in the purification, characterization and structure determination of lipases. Lipids 23, 1101-1106.
8. Carriere, F., Bezzine, S., Verger, R., 1997. Molecular evolution of the pancreatic lipase and two related enzymes towards different substrate selectivities. Journal of Molecular Catalysis B: Enzymatic 3, 55-64.
9. Carriere, F., Withers-Martinez, C., Van Tilbeurgh, H., Roussel, A., Cambillau, C., Verger, R., 1998. Structural basis of the substrate selectivity of pancreatic lipases and some related proteins. Biochim. Biophys. Acta Rev. Biomembr. 1376, 417-432.
10. Hirata, K., Dichek, H. L., Cioffi, J. A., Choi, S. Y., Leeper, N. J., Quintana, L., Kronmal, G. S., Cooper, A. D., Quertermous, T., 1999. Cloning of a unique lipase from endothelial cells extends the lipase gene family. J. Biol. Chem. 274, 14170-14175.
11. Anderson, R. A., Sando, G. N., 1991. Cloning and expression of cDNA encoding human lysosomal acid lipase/cholesteryl ester hydrolase. Similarities to gastric and lingual lipases. J. Biol. Chem. 266, 22479-22484.
12. Carriere, F., Gargouri, Y., Moreau, H., Ransac, S., Rogaiska, E., Verger, R., 1994. Gastric lipases: cellular, biochemical and kinetic aspects. In: Woolley, P., Peterson, S. B. (Eds.), Lipases—their structure, biochemistry, and application, Cambridge University Press, Cambridge, pp. 181-205.
13. Moreau, H., Gargouri, Y., Lecat, D., Junien, J. L., Verger, R., 1988. Screening of preduodenal lipases in several mammals. Biochim. Biophys. Acta 959, 247-252.
14. Carriere, F., Barrowman, J. A., Verger, R., Laugier, R., 1993a. Secretion and contribution to lipolysis of gastric and pancreatic lipases during a test meal in humans. Gastroenterol. 105, 876-888.
15. Carriere, F., Laugier, R., Barrowman, J. A., Douchet, I., Priymenko, N.,
Verger, R., 1993b. Gastric and pancreatic lipase levels during a test meal in dogs. Scand. J. Gastroenterol. 28, 443-454.
16. Carriere, F., Moreau, H., Raphel, V., Laugier, R., Benicourt, C., Junien, J.-L., Verger, R., 1991. Purification and biochemical characterization of dog gastric lipase. Eur. J. Biochem. 202, 75-83.
17. Steiner, J. M., Berridge, B. R., Wojcieszyn, J., Williams, D. A., 2002. Cellular immunolocalization of gastric and pancreatic lipase in various tissues obtained from dogs. Am. J. Vet. Res. 63, 722-727.
18. Steiner, J. M., Broussard, J., Mansfield, C. S., Gumminger, S. R., Williams, D. A. 2001a. Serum canine pancreatic lipase immunoreactivity (cPLI) concentrations in dogs with spontaneous pancreatitis. J. Vet. Int. Med. 15, 274.
19. Steiner, J. M., Gumminger, S. R., Rutz, G. M., Williams, D. A. 2000b. Serum canine pancreatic lipase immunoreactivity (cPLI) concentrations in dogs with exocrine pancreatic insufficiency. J. Vet. Int. Med. 15, 274.
20. Steiner, J. M., Gumminger, S. R., Williams, D. A. 2000 c. Development and validation of an enzyme-linked immunosorbent assay (ELISA) for the measurement of canine pancreatic lipase immunoreactivity (cPLI) in serum. J. Vet. Int. Med. 15, 311.

21. Vandermeers, A., Chroistophe, J., 1968. Alpha-amylase and lipase of rat pancreas. Chromatographic purification and research on molecular weight and amino acid composition. Biochim. Biophys. Acta 154, 110-129.

22. Rathelot, J., Julien, R., Bosc-Bierne, I., Gargouri, Y., Canioni, P., Sarda, L., 1981. Horse pancreatic lipase. Interaction with colipase from various species. Biochimie 63, 227-234.

23. Bosc-Bierne, I., Rathelot, J., Perrot, C., Sarda, L., 1984. Studies on chicken pancreatic lipase and colipase. Biochim. Biophys. Acta 794, 65-71.

24. Gieseg, S. P., Forrester, I. T., Carne, A., 1992. The purification of ovine pancreatic lipase that is free of colipase using an improved delipidation method. Pancreas 7, 45-51.

25. Mejdoub, H., Reinbolt, J., Gargouri, Y., 1994. Dromedary pancreatic lipase: Purification and structural properties. Biochem. Biophys. Acta. Lipids Lipid Metab. 1213, 119-126.

26. Ausubel et al., Current Protocols in Molecular Biology, 1992

27. Lesk, A. M., ed., Oxford University Press, New York, 1988; Biocomputing: Informatics and Genome Projects.

28. Smith, D. W., ed., Academic Press, New York, 1993; Computer Analysis of sequence Data, Part 1.

29. Griffin, A. M., and Griffin, H. G., eds., Humana Press, New Jersey, 1994; Sequence Analysis in Molecular Biology.

30. von Heinje, G., Academic Press, 1987; and Sequence Analysis Primer, Gribskov, M. and Devereux, J., eds., M Stockton Press, New York, 1991.

31. Gribskov, M. and Devereux, J., eds., M Stockton Press, New York, 1991

32. Needleman and Wunsch (J. Mol. Biol. (48):444-453 (1970).

33. Devereux, J., et al, Nucleic Acids Res. 12(1):387 (1984).

34. E. Myers and W. Miller (CABIOS, 4:11-17 (1989).

35. Altschul, et al. (J. Mol. Biol. 215:403-10 (1990).

36. Altschul et al. (Nucleic Acids Res. 25(17):3389-3402 (1997).

37. Bowie et al., Science 247:1306-1310 (1990).

38. Cunningham et al., Science 244:1081-1085 (1989)

39. Smith et al., J. Mol. Biol. 224:899-904 (1992)

40. de Vos et al. Science 255:306-312 (1992).

41. Proteins—Structure and Molecular Properties, 2nd Ed., T. E. Creighton, W. H. Freeman and Company, New York (1993).

42. Wold, F., Posttranslational Covalent Modification of Proteins, B. C. Johnson, Ed., Academic Press, New York 1-12 (1983);

43. Seifter et al. (Meth. Enzymol. 182: 626-646 (1990)).

44. Rattan et al. (Ann. N.Y. Acad. Sci. 663:48-62 (1992).

45. Current Protocols in Molecular Biology, John Wiley & Sons, N.Y. (1989).

46. Nielsen, et al, Science 254:1497-1500 (1991).

47. Sambrook et al., Molecular Cloning: A Laboratory Manual. 2nd. ed., Cold Spring Harbor Laboratory Press, Cold Spring Harbor, N.Y., (1989).

48. Smith et al., Gene 67:31-40 (1988)), pMAL (New England Biolabs, Beverly, Mass.) and pRIT5 (Pharmacia, Piscataway, N.J.)

49. Amann et al., Gene 69:301-315 (1988)

50. Studier et al., Gene Expression Technology: Methods in Enzymology 185:60-89 (1990).

51. Gottesman, S., Gene Expression Technology: Methods in Enzymology 185, Academic Press, San Diego, Calif. (1990)119-128).

52. Wada et al., Nucleic Acids Res. 20:2111-2118 (1992).

53. Baldari, et al., EMBO J. 6:229-234 (1987).

54. Kurjan et al., Cell 30:933-943(1982).

55. Schultz et al., Gene 54:113-123 (1987).

56. Smith et al., Mol. Cell Biol. 3:2156-2165 (1983).

57. Lucklow et al., Virology 170:31-39 (1989).

58. Seed, B. Nature 329:840(1987).

59. Kaufman et al., EMBO J. 6:187-195 (1987).

60. Chibata, Ichiro, Halsted Press, NY (1978) Immobilized Enzymes.

61. Cuatrecasas, J. Biol. Chem, 245:3059 (1970).

62. Steiner, J. M., Williams, D. A., 2002. Purification of classical pancreatic lipase from dog pancreas. Biochimie 84 (2002) 1243-1251.

63. Thirstrup, K., et al FEBS, 1993.

64. Ulmer, J. B., et al Science, 1993.

65. Harlow, Antibodies, Cold Spring Harbor Press, (1988) pp. 53-135.

66. Harlow, Antibodies, Cold Spring Harbor Press, (1988) pp. 139-238.

67. Steiner, et al. Can. J. Vet Res. 67:175-82.

What is claimed is:

1. A method for determining the presence or amount of canine pancreatic lipase in a biological sample comprising:
   (a) contacting the sample with a first monoclonal antibody that specifically binds canine pancreatic lipase; and
   (b) detecting the binding of the canine pancreatic lipase in the sample to the first monoclonal antibody,
   wherein the first monoclonal antibody is the monoclonal antibody produced by hybridoma cell line designated under the ATCC deposit No. PTA-6652 or PTA-6653, or a monoclonal antibody that competes for the epitope that binds the monoclonal antibody produced by hybridoma cell line PTA-6652 or PTA-6653 on canine pancreatic lipase.

2. The method of claim 1 wherein the first monoclonal antibody is the antibody produced by hybridoma cell line PTA-6652 or the antibody produced by hybridoma cell line PTA-6653.

3. The method of claim 1 further comprising contacting a standard comprising recombinant canine pancreatic lipase with the first monoclonal antibody, detecting the binding of the standard to the first monoclonal antibody, and comparing the amount of binding of the first monoclonal antibody to the canine pancreatic lipase in the sample to the amount of binding of the first monoclonal antibody to the standard.

4. The method of claim 1 wherein the first monoclonal antibody is conjugated to a label.

5. The method of claim 1 wherein the first monoclonal antibody is directly or indirectly immobilized on a solid phase.

6. The method of claim 5 wherein the detecting further comprises: contacting the solid phase with a second antibody specific for canine pancreatic lipase, wherein the second antibody is directly or indirectly conjugated to a label; and detecting the label bound to the solid phase, wherein the first monoclonal antibody and the second antibody do not compete for binding to the same epitope on canine pancreatic lipase.

7. The method of claim 6 further comprising contacting a standard comprising recombinant canine pancreatic lipase with the first monoclonal antibody and the second antibody, and comparing a signal from the label of the second antibody that is bound to the canine pancreatic lipase in the sample to the signal from the label of the second antibody that is bound to the standard.

8. The method of claim 7 wherein the second antibody is a second monoclonal antibody.

9. The method of claim 8 wherein the second monoclonal antibody is produced by hybridoma cell line designated under the ATCC Patent Deposit No. PTA-6652 or PTA-6653, or a monoclonal antibody that competes for the epitope that binds the antibody produced by hybridoma cell line PTA-6652 or the antibody produced by hybridoma cell line PTA-6653 on canine pancreatic lipase, and wherein the first monoclonal antibody and the second monoclonal antibody do not compete for binding to the same epitope on canine pancreatic lipase.

10. The method of claim 9, wherein the first monoclonal antibody is the antibody produced by hybridoma cell line PTA-6652 and the second monoclonal antibody is the antibody produced by hybridoma cell line PTA-6653.

11. The method of claim 9, wherein the first monoclonal antibody is the antibody produced by hybridoma cell line PTA-6653 and the second monoclonal antibody is the antibody produced by hybridoma cell line PTA-6652.

12. A method for determining the presence or amount of canine pancreatic lipase in a biological sample comprising:
(a) forming a mixture of the sample with a first monoclonal antibody that specifically binds canine pancreatic lipase, wherein the first monoclonal antibody is conjugated to a label;
(b) allowing the canine pancreatic lipase in the sample and the first monoclonal antibody to form a complex;
(c) contacting the mixture with a second monoclonal antibody that binds to canine pancreatic lipase wherein the second monoclonal antibody is immobilized on a solid phase; and
(d) detecting the presence or amount of the label on the solid phase, wherein at least one of the first monoclonal antibody and the second monoclonal antibody is the antibody produced by hybridoma cell line designated under the ATCC Patent Deposit No. PTA-6652 or PTA-6653, or a monoclonal antibody that competes for the epitope that binds the antibody produced by hybridoma cell line PTA-6652 or the antibody produced by hybridoma cell line PTA-6653 on canine pancreatic lipase, and wherein the first monoclonal antibody and the second monoclonal antibody do not compete for binding to the same epitope on canine pancreatic lipase.

13. The method of claim 12, wherein the first monoclonal antibody is the antibody produced by hybridoma cell line PTA-6652 and the second monoclonal antibody is the antibody produced by hybridoma cell line PTA-6653.

14. The method of claim 12, wherein the first monoclonal antibody is the antibody produced by hybridoma cell line PTA-6653 and the second monoclonal antibody is the antibody produced by hybridoma cell line PTA-6652.

15. A method for determining the presence or amount of canine pancreatic lipase in a biological sample comprising:
(a) forming a mixture of the sample with a first monoclonal antibody that specifically binds canine pancreatic lipase, wherein the first monoclonal antibody is conjugated to a first label;
(b) allowing the canine pancreatic lipase in the sample and the first monoclonal antibody to form a complex;
(c) contacting the mixture with a second monoclonal antibody that specifically binds to canine pancreatic lipase, wherein the second monoclonal antibody is conjugated to a second label; and
(d) detecting the association of the labels with the complex, thereby detecting the presence of canine pancreatic lipase in the sample, wherein at least one of the first monoclonal antibody and the second monoclonal antibody is the antibody produced by hybridoma cell line designated under the ATCC Patent Deposit No. PTA-6652 or PTA-6653, or a monoclonal antibody that competes for the epitope that binds the antibody produced by hybridoma cell line PTA-6652 or the antibody produced by hybridoma cell line PTA-6653 on canine pancreatic lipase, and wherein the first monoclonal antibody and the second monoclonal antibody do not compete for binding to the same epitope on canine pancreatic lipase.

16. The method of claim 15, wherein the first monoclonal antibody is the antibody produced by hybridoma cell line PTA-6652 and the second monoclonal antibody is the antibody produced by hybridoma cell line PTA-6653.

17. The method of claim 15, wherein the first monoclonal antibody is the antibody produced by hybridoma cell line PTA-6653 and the second monoclonal antibody is the antibody produced by hybridoma cell line PTA-6652

* * * * *

SEQUENCE LISTING

```
<160> NUMBER OF SEQ ID NOS: 52

<210> SEQ ID NO 1
<211> LENGTH: 25
<212> TYPE: PRT
<213> ORGANISM: Canis sp.
<220> FEATURE:
<221> NAME/KEY: MISC_FEATURE
<223> OTHER INFORMATION: The N-terminal amino acid sequence from
      purified canine pancreatic lipase.

<400> SEQUENCE: 1

Lys Glu Val Cys Phe Pro Arg Leu Gly Cys Phe Ser Asp Asp Ser Pro
1               5                   10                  15

Trp Ala Gly Ile Val Glu Arg Pro Leu
            20                  25
```

```
<210> SEQ ID NO 2
<211> LENGTH: 1429
<212> TYPE: DNA
<213> ORGANISM: Canis sp.
<220> FEATURE:
<221> NAME/KEY: misc_feature
<223> OTHER INFORMATION: The 1.429Kb canine pancreatic lipase gene
      designated cPL1.

<400> SEQUENCE: 2
ggtgcgtgga acccaacgga actgccacga tgctgctaat ctggacacta tcactgctgc    60
tgggagcagt agtaggaaaa gaagtctgct tcccaagact tggctgtttt agtgatgact   120
ccccatgggc aggaattgtg gagagacccc tcaaaatatt gccctgggct ccaaaagatg   180
tcaatacccg cttactccta tacactaacg agaacccaga taactttcaa gaacttactg   240
cagatccatc aattatcaca agctccagtt tcaaaacaga tagaaaaacc cgctttatta   300
ttcatggatt catagacaag ggagaagaaa gctggttggc caacatgtgc aagaaaatgt   360
ttgtagtgga aagtgtgaac tgcatctgtg tggactggaa gagtggctcc cgaactggtt   420
acactcaggc ctcgcagaac atccggatcg tgggggcaga agtggcatat tttgttgaag   480
ttcttcagtc agcatttggg tactcgcctt ccgacgtcca tcattggc cacagcctgg     540 gagcccacgc agctggggag gcaggaagga ggctcaatgg cactgcagga cgaatcacag   600
ggttggatcc agctgaacct tgctttgagg gcacacccga attagtccga ttggacccca   660
gcgatgccca gtttgtggat gtaattcaca cagatgctgc ccctataatc cccaacatgg   720
ggtttggaat gagtcaaact gtaggccacc tagatttctt tccaaatgga ggaaaagaaa   780
tgcctggatg tcagaagaat attctctctc agattgttga catagatggg atctgggaag   840
ggactcgtga ctttgtggcc tgtaatcact aagaagttca agtattac tctgatagca     900 tcctcaaccc tgacggcttt gctggattcc cttgtgcctc ttacaatgtt tcactgcaa    960 acaagtgctt cccctgccca agcgaaggct gcccacagat gggtcattat gctgacagat   1020
ttcctggaaa aactgacaaa gtgaaccaga tattctatct agacactggt gatgccagca   1080
attttgcccg ttggaggtat aaggtagctg tcacactgtc tggaagaag gttacaggac    1140 acgtgctagt ttctctgttt ggaaataaag gaaattctaa acagtatgaa attttcaagg   1200
gcactctcca accagagagc actcattcca atgaatttga ctctgatgtg gaagttggag   1260
atgtgcagaa ggttaaattt gtttggtaca acaatgtgat caacccaact ctacccagag   1320
tgggagcatc aagatcaca gtggaaagaa atgatgggaa atattcaac ttctgtagta     1380 aagaaaccgt gagggaagat attttactta ctcttacccc atgttaaga               1429

<210> SEQ ID NO 3
<211> LENGTH: 465
<212> TYPE: PRT
<213> ORGANISM: Canis sp.
<220> FEATURE:
<221> NAME/KEY: MISC_FEATURE
<223> OTHER INFORMATION: The translated canine pancreatic lipase protein
      designated cPLP1 deduced from the cDNA sequence.

<400> SEQUENCE: 3

Met Leu Leu Ile Trp Thr Leu Ser Leu Leu Leu Gly Ala Val Val Gly
1               5                   10                  15

Lys Glu Val Cys Phe Pro Arg Leu Gly Cys Phe Ser Asp Asp Ser Pro
            20                  25                  30

Trp Ala Gly Ile Val Glu Arg Pro Leu Lys Ile Leu Pro Trp Ala Pro
        35                  40                  45
```

-continued

```
Lys Asp Val Asn Thr Arg Leu Leu Tyr Thr Asn Glu Asn Pro Asp
 50                  55                  60

Asn Phe Gln Glu Leu Thr Ala Asp Pro Ser Ile Ile Thr Ser Ser
 65                  70                  75                  80

Phe Lys Thr Asp Arg Lys Thr Arg Phe Ile Ile Gly Phe Ile Asp
                 85                  90                  95

Lys Gly Glu Glu Ser Trp Leu Ala Asn Met Cys Lys Lys Met Phe Val
             100                 105                 110

Val Glu Ser Val Asn Cys Ile Cys Val Asp Trp Lys Ser Gly Ser Arg
             115                 120                 125

Thr Gly Tyr Thr Gln Ala Ser Gln Asn Ile Arg Ile Val Gly Ala Glu
         130                 135                 140

Val Ala Tyr Phe Val Glu Val Leu Gln Ser Ala Phe Gly Tyr Ser Pro
145                 150                 155                 160

Ser Asp Val His Ile Ile Gly His Ser Leu Gly Ala His Ala Ala Gly
                 165                 170                 175

Glu Ala Gly Arg Arg Leu Asn Gly Thr Ala Gly Arg Ile Thr Gly Leu
             180                 185                 190

Asp Pro Ala Glu Pro Cys Phe Glu Gly Thr Pro Glu Leu Val Arg Leu
         195                 200                 205

Asp Pro Ser Asp Ala Gln Phe Val Asp Val Ile His Thr Asp Ala Ala
         210                 215                 220

Pro Ile Ile Pro Asn Met Gly Phe Gly Met Ser Gln Thr Val Gly His
225                 230                 235                 240

Leu Asp Phe Phe Pro Asn Gly Gly Lys Glu Met Pro Gly Cys Gln Lys
                 245                 250                 255

Asn Ile Leu Ser Gln Ile Val Asp Ile Asp Gly Ile Trp Glu Gly Thr
             260                 265                 270

Arg Asp Phe Val Ala Cys Asn His Leu Arg Ser Tyr Lys Tyr Tyr Ser
         275                 280                 285

Asp Ser Ile Leu Asn Pro Asp Gly Phe Ala Gly Phe Pro Cys Ala Ser
     290                 295                 300

Tyr Asn Val Phe Thr Ala Asn Lys Cys Phe Pro Cys Pro Ser Glu Gly
305                 310                 315                 320

Cys Pro Gln Met Gly His Tyr Ala Asp Arg Phe Pro Gly Lys Thr Asp
                 325                 330                 335

Lys Val Asn Gln Ile Phe Tyr Leu Asp Thr Gly Asp Ala Ser Asn Phe
             340                 345                 350

Ala Arg Trp Arg Tyr Lys Val Ala Val Thr Leu Ser Gly Lys Lys Val
         355                 360                 365

Thr Gly His Val Leu Val Ser Leu Phe Gly Asn Lys Gly Asn Ser Lys
     370                 375                 380

Gln Tyr Glu Ile Phe Lys Gly Thr Leu Gln Pro Glu Ser Thr His Ser
385                 390                 395                 400

Asn Glu Phe Asp Ser Asp Val Glu Val Gly Asp Val Gln Lys Val Lys
                 405                 410                 415

Phe Val Trp Tyr Asn Asn Val Ile Asn Pro Thr Leu Pro Arg Val Gly
             420                 425                 430

Ala Ser Lys Ile Thr Val Glu Arg Asn Asp Gly Lys Ile Phe Asn Phe
         435                 440                 445

Cys Ser Lys Glu Thr Val Arg Glu Asp Ile Leu Leu Thr Leu Thr Pro
     450                 455                 460
```

Cys
465

<210> SEQ ID NO 4
<211> LENGTH: 29
<212> TYPE: DNA
<213> ORGANISM: Canis sp.
<220> FEATURE:
<221> NAME/KEY: misc_feature
<223> OTHER INFORMATION: A degenerate primer for 3'RACE (UPM-universal
      primer mix, Clontech) and nested PCR.
<220> FEATURE:
<221> NAME/KEY: misc_feature
<223> OTHER INFORMATION: Symbol s is g or c; y is t/u or c; h is a or c
      or t/u; and m is a or c.

<400> SEQUENCE: 4
gtggccggca aggaggtstg yttycchmg                              29

<210> SEQ ID NO 5
<211> LENGTH: 30
<212> TYPE: DNA
<213> ORGANISM: Canis sp.
<220> FEATURE:
<221> NAME/KEY: misc_feature
<223> OTHER INFORMATION: A degenerate primer for 3'RACE (UPM-universal
      primer mix, Clontech) and nested PCR.
<220> FEATURE:
<221> NAME/KEY: misc_feature
<223> OTHER INFORMATION: Symbol s is g or c; y is t/u or c; and b is g
      or c or t/u.

<400> SEQUENCE: 5
ggtgttcagg tagaacacyt gbccsacbyc                             30

<210> SEQ ID NO 6
<211> LENGTH: 29
<212> TYPE: DNA
<213> ORGANISM: Canis sp.
<220> FEATURE:
<221> NAME/KEY: misc_feature
<223> OTHER INFORMATION: A degenerate primer for 3'RACE (UPM-universal
      primer mix, Clontech) and nested PCR.
<220> FEATURE:
<221> NAME/KEY: misc_feature
<223> OTHER INFORMATION: Symbol s is g or c; y is t/u or c; and v is a
      or g or c.

<400> SEQUENCE: 6
gacgacagcc cctgggcygg vatygtsga                              29

<210> SEQ ID NO 7
<211> LENGTH: 27
<212> TYPE: DNA
<213> ORGANISM: Canis sp.
<220> FEATURE:
<221> NAME/KEY: misc_feature
<223> OTHER INFORMATION: A degenerate primer for 5'RACE (UPM-universal
      primer mix, Clontech) and nested PCR.

<400> SEQUENCE: 7
ctgcccccac gatccggatg ttctgcg                                27

<210> SEQ ID NO 8
<211> LENGTH: 30
<212> TYPE: DNA
<213> ORGANISM: Canis sp.
<220> FEATURE:
<221> NAME/KEY: misc_feature
<223> OTHER INFORMATION: A degenerate primer for 3'RACE (UPM-universal

```
       primer mix, Clontech) and nested PCR.
<220> FEATURE:
<221> NAME/KEY: misc_feature
<223> OTHER INFORMATION: Symbol s is g or c; y is t/u or c; r is g or a;
      and h is a or c or t/u.

<400> SEQUENCE: 8
gatcctgccc tggagccchr aggaygtsra                                          30

<210> SEQ ID NO 9
<211> LENGTH: 29
<212> TYPE: DNA
<213> ORGANISM: Canis sp.
<220> FEATURE:
<221> NAME/KEY: misc_feature
<223> OTHER INFORMATION: A degenerate primer for 5'RACE (UPM-universal
      primer mix, Clontech) and nested PCR.

<400> SEQUENCE: 9
ctggagcttg tgataattga tggatctgc                                           29

<210> SEQ ID NO 10
<211> LENGTH: 20
<212> TYPE: PRT
<213> ORGANISM: Canis sp.
<220> FEATURE:
<221> NAME/KEY: MISC_FEATURE
<223> OTHER INFORMATION: Canine pancreatic lipase peptide which is a
      20-mer peptide spanning the canine pancreatic lipase protein cPLP1
      in 10 amino acid sequence overlap.

<400> SEQUENCE: 10

Phe Ser Asp Asp Ser Pro Trp Ala Gly Ile Val Glu Arg Pro Leu Lys
1               5                   10                  15

Ile Leu Pro Trp
            20

<210> SEQ ID NO 11
<211> LENGTH: 20
<212> TYPE: PRT
<213> ORGANISM: Canis sp.
<220> FEATURE:
<221> NAME/KEY: MISC_FEATURE
<223> OTHER INFORMATION: Canine pancreatic lipase peptide which is a
      20-mer peptide spanning the canine pancreatic lipase protein cPLP1
      in 10 amino acid sequence overlap.

<400> SEQUENCE: 11

Val Glu Arg Pro Leu Lys Ile Leu Pro Trp Ala Pro Lys Asp Val Asn
1               5                   10                  15

Thr Arg Leu Leu
            20

<210> SEQ ID NO 12
<211> LENGTH: 20
<212> TYPE: PRT
<213> ORGANISM: Canis sp.
<220> FEATURE:
<221> NAME/KEY: MISC_FEATURE
<223> OTHER INFORMATION: Canine pancreatic lipase peptide which is a
      20-mer peptide spanning the canine pancreatic lipase protein cPLP1
      in 10 amino acid sequence overlap.

<400> SEQUENCE: 12

Ala Pro Lys Asp Val Asn Thr Arg Leu Leu Leu Tyr Thr Asn Glu Asn
1               5                   10                  15

Pro Asp Asn Phe
```

-continued

```
<210> SEQ ID NO 13
<211> LENGTH: 20
<212> TYPE: PRT
<213> ORGANISM: Canis sp.
<220> FEATURE:
<221> NAME/KEY: MISC_FEATURE
<223> OTHER INFORMATION: Canine pancreatic lipase peptide which is a
      20-mer peptide spanning the canine pancreatic lipase protein cPLP1
      in 10 amino acid sequence overlap.

<400> SEQUENCE: 13

Leu Tyr Thr Asn Glu Asn Pro Asp Asn Phe Gln Glu Leu Thr Ala Asp
1               5                   10                  15

Pro Ser Ile Ile
            20

<210> SEQ ID NO 14
<211> LENGTH: 20
<212> TYPE: PRT
<213> ORGANISM: Canis sp.
<220> FEATURE:
<221> NAME/KEY: MISC_FEATURE
<223> OTHER INFORMATION: Canine pancreatic lipase peptide which is a
      20-mer peptide spanning the canine pancreatic lipase protein cPLP1
      in 10 amino acid sequence overlap.

<400> SEQUENCE: 14

Gln Glu Leu Thr Ala Asp Pro Ser Ile Ile Thr Ser Ser Ser Phe Lys
1               5                   10                  15

Thr Asp Arg Lys
            20

<210> SEQ ID NO 15
<211> LENGTH: 20
<212> TYPE: PRT
<213> ORGANISM: Canis sp.
<220> FEATURE:
<221> NAME/KEY: MISC_FEATURE
<223> OTHER INFORMATION: Canine pancreatic lipase peptide which is a
      20-mer peptide spanning the canine pancreatic lipase protein cPLP1
      in 10 amino acid sequence overlap.

<400> SEQUENCE: 15

Thr Ser Ser Ser Phe Lys Thr Asp Arg Lys Thr Arg Phe Ile Ile His
1               5                   10                  15

Gly Phe Ile Asp
            20

<210> SEQ ID NO 16
<211> LENGTH: 20
<212> TYPE: PRT
<213> ORGANISM: Canis sp.
<220> FEATURE:
<221> NAME/KEY: MISC_FEATURE
<223> OTHER INFORMATION: Canine pancreatic lipase peptide which is a
      20-mer peptide spanning the canine pancreatic lipase protein cPLP1
      in 10 amino acid sequence overlap.

<400> SEQUENCE: 16

Thr Arg Phe Ile Ile His Gly Phe Ile Asp Lys Gly Glu Glu Ser Trp
1               5                   10                  15

Leu Ala Asn Met
            20
```

```
<210> SEQ ID NO 17
<211> LENGTH: 20
<212> TYPE: PRT
<213> ORGANISM: Canis sp.
<220> FEATURE:
<221> NAME/KEY: MISC_FEATURE
<223> OTHER INFORMATION: Canine pancreatic lipase peptide which is a
      20-mer peptide spanning the canine pancreatic lipase protein cPLP1
      in 10 amino acid sequence overlap.

<400> SEQUENCE: 17

Lys Gly Glu Glu Ser Trp Leu Ala Asn Met Cys Lys Lys Met Phe Val
1               5                   10                  15

Val Glu Ser Val
            20

<210> SEQ ID NO 18
<211> LENGTH: 20
<212> TYPE: PRT
<213> ORGANISM: Canis sp.
<220> FEATURE:
<221> NAME/KEY: MISC_FEATURE
<223> OTHER INFORMATION: Canine pancreatic lipase peptide which is a
      20-mer peptide spanning the canine pancreatic lipase protein cPLP1
      in 10 amino acid sequence overlap.

<400> SEQUENCE: 18

Cys Lys Lys Met Phe Val Val Glu Ser Val Asn Cys Ile Cys Val Asp
1               5                   10                  15

Trp Lys Ser Gly
            20

<210> SEQ ID NO 19
<211> LENGTH: 20
<212> TYPE: PRT
<213> ORGANISM: Canis sp.
<220> FEATURE:
<221> NAME/KEY: MISC_FEATURE
<223> OTHER INFORMATION: Canine pancreatic lipase peptide which is a
      20-mer peptide spanning the canine pancreatic lipase protein cPLP1
      in 10 amino acid sequence overlap.

<400> SEQUENCE: 19

Asn Cys Ile Cys Val Asp Trp Lys Ser Gly Ser Arg Thr Gly Tyr Thr
1               5                   10                  15

Gln Ala Ser Gln
            20

<210> SEQ ID NO 20
<211> LENGTH: 20
<212> TYPE: PRT
<213> ORGANISM: Canis sp.
<220> FEATURE:
<221> NAME/KEY: MISC_FEATURE
<223> OTHER INFORMATION: Canine pancreatic lipase peptide which is a
      20-mer peptide spanning the canine pancreatic lipase protein cPLP1
      in 10 amino acid sequence overlap.

<400> SEQUENCE: 20

Ser Arg Thr Gly Tyr Thr Gln Ala Ser Gln Asn Ile Arg Ile Val Gly
1               5                   10                  15

Ala Glu Val Ala
            20

<210> SEQ ID NO 21
<211> LENGTH: 20
<212> TYPE: PRT
```

```
<213> ORGANISM: Canis sp.
<220> FEATURE:
<221> NAME/KEY: MISC_FEATURE
<223> OTHER INFORMATION: Canine pancreatic lipase peptide which is a
      20-mer peptide spanning the canine pancreatic lipase protein cPLP1
      in 10 amino acid sequence overlap.

<400> SEQUENCE: 21

Asn Ile Arg Ile Val Gly Ala Glu Val Ala Tyr Phe Val Glu Val Leu
1               5                   10                  15

Gln Ser Ala Phe
            20

<210> SEQ ID NO 22
<211> LENGTH: 20
<212> TYPE: PRT
<213> ORGANISM: Canis sp.
<220> FEATURE:
<221> NAME/KEY: MISC_FEATURE
<223> OTHER INFORMATION: Canine pancreatic lipase peptide which is a
      20-mer peptide spanning the canine pancreatic lipase protein cPLP1
      in 10 amino acid sequence overlap.

<400> SEQUENCE: 22

Tyr Phe Val Glu Val Leu Gln Ser Ala Phe Gly Tyr Ser Pro Ser Asp
1               5                   10                  15

Val His Ile Ile
            20

<210> SEQ ID NO 23
<211> LENGTH: 20
<212> TYPE: PRT
<213> ORGANISM: Canis sp.
<220> FEATURE:
<221> NAME/KEY: MISC_FEATURE
<223> OTHER INFORMATION: Canine pancreatic lipase peptide which is a
      20-mer peptide spanning the canine pancreatic lipase protein cPLP1
      in 10 amino acid sequence overlap.

<400> SEQUENCE: 23

Gly Tyr Ser Pro Ser Asp Val His Ile Ile Gly His Ser Leu Gly Ala
1               5                   10                  15

His Ala Ala Gly
            20

<210> SEQ ID NO 24
<211> LENGTH: 20
<212> TYPE: PRT
<213> ORGANISM: Canis sp.
<220> FEATURE:
<221> NAME/KEY: MISC_FEATURE
<223> OTHER INFORMATION: Canine pancreatic lipase peptide which is a
      20-mer peptide spanning the canine pancreatic lipase protein cPLP1
      in 10 amino acid sequence overlap.

<400> SEQUENCE: 24

Gly His Ser Leu Gly Ala His Ala Ala Gly Glu Ala Gly Arg Arg Leu
1               5                   10                  15

Asn Gly Thr Ala
            20

<210> SEQ ID NO 25
<211> LENGTH: 20
<212> TYPE: PRT
<213> ORGANISM: Canis sp.
<220> FEATURE:
<221> NAME/KEY: MISC_FEATURE
```

```
<223> OTHER INFORMATION: Canine pancreatic lipase peptide which is a
      20-mer peptide spanning the canine pancreatic lipase protein cPLP1
      in 10 amino acid sequence overlap.

<400> SEQUENCE: 25

Glu Ala Gly Arg Arg Leu Asn Gly Thr Ala Gly Arg Ile Thr Gly Leu
1               5                   10                  15

Asp Pro Ala Glu
            20

<210> SEQ ID NO 26
<211> LENGTH: 20
<212> TYPE: PRT
<213> ORGANISM: Canis sp.
<220> FEATURE:
<221> NAME/KEY: MISC_FEATURE
<223> OTHER INFORMATION: Canine pancreatic lipase peptide which is a
      20-mer peptide spanning the canine pancreatic lipase protein cPLP1
      in 10 amino acid sequence overlap.

<400> SEQUENCE: 26

Gly Arg Ile Thr Gly Leu Asp Pro Ala Glu Pro Cys Phe Glu Gly Thr
1               5                   10                  15

Pro Glu Leu Val
            20

<210> SEQ ID NO 27
<211> LENGTH: 20
<212> TYPE: PRT
<213> ORGANISM: Canis sp.
<220> FEATURE:
<221> NAME/KEY: MISC_FEATURE
<223> OTHER INFORMATION: Canine pancreatic lipase peptide which is a
      20-mer peptide spanning the canine pancreatic lipase protein cPLP1
      in 10 amino acid sequence overlap.

<400> SEQUENCE: 27

Pro Cys Phe Glu Gly Thr Pro Glu Leu Val Arg Leu Asp Pro Ser Asp
1               5                   10                  15

Ala Gln Phe Val
            20

<210> SEQ ID NO 28
<211> LENGTH: 20
<212> TYPE: PRT
<213> ORGANISM: Canis sp.
<220> FEATURE:
<221> NAME/KEY: MISC_FEATURE
<223> OTHER INFORMATION: Canine pancreatic lipase peptide which is a
      20-mer peptide spanning the canine pancreatic lipase protein cPLP1
      in 10 amino acid sequence overlap.

<400> SEQUENCE: 28

Arg Leu Asp Pro Ser Asp Ala Gln Phe Val Asp Val Ile His Thr Asp
1               5                   10                  15

Ala Ala Pro Ile
            20

<210> SEQ ID NO 29
<211> LENGTH: 20
<212> TYPE: PRT
<213> ORGANISM: Canis sp.
<220> FEATURE:
<221> NAME/KEY: MISC_FEATURE
<223> OTHER INFORMATION: Canine pancreatic lipase peptide which is a
      20-mer peptide spanning the canine pancreatic lipase protein cPLP1
      in 10 amino acid sequence overlap.
```

```
<400> SEQUENCE: 29

Asp Val Ile His Thr Asp Ala Ala Pro Ile Ile Pro Asn Met Gly Phe
1               5                   10                  15

Gly Met Ser Gln
            20

<210> SEQ ID NO 30
<211> LENGTH: 20
<212> TYPE: PRT
<213> ORGANISM: Canis sp.
<220> FEATURE:
<221> NAME/KEY: MISC_FEATURE
<223> OTHER INFORMATION: Canine pancreatic lipase peptide which is a
      20-mer peptide spanning the canine pancreatic lipase protein cPLP1
      in 10 amino acid sequence overlap.

<400> SEQUENCE: 30

Ile Pro Asn Met Gly Phe Gly Met Ser Gln Thr Val Gly His Leu Asp
1               5                   10                  15

Phe Phe Pro Asn
            20

<210> SEQ ID NO 31
<211> LENGTH: 20
<212> TYPE: PRT
<213> ORGANISM: Canis sp.
<220> FEATURE:
<221> NAME/KEY: MISC_FEATURE
<223> OTHER INFORMATION: Canine pancreatic lipase peptide which is a
      20-mer peptide spanning the canine pancreatic lipase protein cPLP1
      in 10 amino acid sequence overlap.

<400> SEQUENCE: 31

Thr Val Gly His Leu Asp Phe Phe Pro Asn Gly Gly Lys Glu Met Pro
1               5                   10                  15

Gly Cys Gln Lys
            20

<210> SEQ ID NO 32
<211> LENGTH: 20
<212> TYPE: PRT
<213> ORGANISM: Canis sp.
<220> FEATURE:
<221> NAME/KEY: MISC_FEATURE
<223> OTHER INFORMATION: Canine pancreatic lipase peptide which is a
      20-mer peptide spanning the canine pancreatic lipase protein cPLP1
      in 10 amino acid sequence overlap.

<400> SEQUENCE: 32

Gly Gly Lys Glu Met Pro Gly Cys Gln Lys Asn Ile Leu Ser Gln Ile
1               5                   10                  15

Val Asp Ile Asp
            20

<210> SEQ ID NO 33
<211> LENGTH: 20
<212> TYPE: PRT
<213> ORGANISM: Canis sp.
<220> FEATURE:
<221> NAME/KEY: MISC_FEATURE
<223> OTHER INFORMATION: Canine pancreatic lipase peptide which is a
      20-mer peptide spanning the canine pancreatic lipase protein cPLP1
      in 10 amino acid sequence overlap.

<400> SEQUENCE: 33
```

```
Asn Ile Leu Ser Gln Ile Val Asp Ile Asp Gly Ile Trp Glu Gly Thr
1               5                   10                  15

Arg Asp Phe Val
            20

<210> SEQ ID NO 34
<211> LENGTH: 20
<212> TYPE: PRT
<213> ORGANISM: Canis sp.
<220> FEATURE:
<221> NAME/KEY: MISC_FEATURE
<223> OTHER INFORMATION: Canine pancreatic lipase peptide which is a
      20-mer peptide spanning the canine pancreatic lipase protein cPLP1
      in 10 amino acid sequence overlap.

<400> SEQUENCE: 34

Gly Ile Trp Glu Gly Thr Arg Asp Phe Val Ala Cys Asn His Leu Arg
1               5                   10                  15

Ser Tyr Lys Tyr
            20

<210> SEQ ID NO 35
<211> LENGTH: 20
<212> TYPE: PRT
<213> ORGANISM: Canis sp.
<220> FEATURE:
<221> NAME/KEY: MISC_FEATURE
<223> OTHER INFORMATION: Canine pancreatic lipase peptide which is a
      20-mer peptide spanning the canine pancreatic lipase protein cPLP1
      in 10 amino acid sequence overlap.

<400> SEQUENCE: 35

Ala Cys Asn His Leu Arg Ser Tyr Lys Tyr Tyr Ser Asp Ser Ile Leu
1               5                   10                  15

Asn Pro Asp Gly
            20

<210> SEQ ID NO 36
<211> LENGTH: 20
<212> TYPE: PRT
<213> ORGANISM: Canis sp.
<220> FEATURE:
<221> NAME/KEY: MISC_FEATURE
<223> OTHER INFORMATION: Canine pancreatic lipase peptide which is a
      20-mer peptide spanning the canine pancreatic lipase protein cPLP1
      in 10 amino acid sequence overlap.

<400> SEQUENCE: 36

Tyr Ser Asp Ser Ile Leu Asn Pro Asp Gly Phe Ala Gly Phe Pro Cys
1               5                   10                  15

Ala Ser Tyr Asn
            20

<210> SEQ ID NO 37
<211> LENGTH: 20
<212> TYPE: PRT
<213> ORGANISM: Canis sp.
<220> FEATURE:
<221> NAME/KEY: MISC_FEATURE
<223> OTHER INFORMATION: Canine pancreatic lipase peptide which is a
      20-mer peptide spanning the canine pancreatic lipase protein cPLP1
      in 10 amino acid sequence overlap.

<400> SEQUENCE: 37

Phe Ala Gly Phe Pro Cys Ala Ser Tyr Asn Val Phe Thr Ala Asn Lys
1               5                   10                  15
```

```
Cys Phe Pro Cys
            20

<210> SEQ ID NO 38
<211> LENGTH: 20
<212> TYPE: PRT
<213> ORGANISM: Canis sp.
<220> FEATURE:
<221> NAME/KEY: MISC_FEATURE
<223> OTHER INFORMATION: Canine pancreatic lipase peptide which is a
      20-mer peptide spanning the canine pancreatic lipase protein cPLP1
      in 10 amino acid sequence overlap.

<400> SEQUENCE: 38

Val Phe Thr Ala Asn Lys Cys Phe Pro Cys Pro Ser Glu Gly Cys Pro
1               5                   10                  15

Gln Met Gly His
            20

<210> SEQ ID NO 39
<211> LENGTH: 20
<212> TYPE: PRT
<213> ORGANISM: Canis sp.
<220> FEATURE:
<221> NAME/KEY: MISC_FEATURE
<223> OTHER INFORMATION: Canine pancreatic lipase peptide which is a
      20-mer peptide spanning the canine pancreatic lipase protein cPLP1
      in 10 amino acid sequence overlap.

<400> SEQUENCE: 39

Pro Ser Glu Gly Cys Pro Gln Met Gly His Tyr Ala Asp Arg Phe Pro
1               5                   10                  15

Gly Lys Thr Asp
            20

<210> SEQ ID NO 40
<211> LENGTH: 20
<212> TYPE: PRT
<213> ORGANISM: Canis sp.
<220> FEATURE:
<221> NAME/KEY: MISC_FEATURE
<223> OTHER INFORMATION: Canine pancreatic lipase peptide which is a
      20-mer peptide spanning the canine pancreatic lipase protein cPLP1
      in 10 amino acid sequence overlap.

<400> SEQUENCE: 40

Tyr Ala Asp Arg Phe Pro Gly Lys Thr Asp Lys Val Asn Gln Ile Phe
1               5                   10                  15

Tyr Leu Asp Thr
            20

<210> SEQ ID NO 41
<211> LENGTH: 20
<212> TYPE: PRT
<213> ORGANISM: Canis sp.
<220> FEATURE:
<221> NAME/KEY: MISC_FEATURE
<223> OTHER INFORMATION: Canine pancreatic lipase peptide which is a
      20-mer peptide spanning the canine pancreatic lipase protein cPLP1
      in 10 amino acid sequence overlap.

<400> SEQUENCE: 41

Lys Val Asn Gln Ile Phe Tyr Leu Asp Thr Gly Asp Ala Ser Asn Phe
1               5                   10                  15

Ala Arg Trp Arg
            20
```

```
<210> SEQ ID NO 42
<211> LENGTH: 20
<212> TYPE: PRT
<213> ORGANISM: Canis sp.
<220> FEATURE:
<221> NAME/KEY: MISC_FEATURE
<223> OTHER INFORMATION: Canine pancreatic lipase peptide which is a
      20-mer peptide spanning the canine pancreatic lipase protein cPLP1
      in 10 amino acid sequence overlap.

<400> SEQUENCE: 42

Gly Asp Ala Ser Asn Phe Ala Arg Trp Arg Tyr Lys Val Ala Val Thr
1               5                   10                  15

Leu Ser Gly Lys
            20

<210> SEQ ID NO 43
<211> LENGTH: 20
<212> TYPE: PRT
<213> ORGANISM: Canis sp.
<220> FEATURE:
<221> NAME/KEY: MISC_FEATURE
<223> OTHER INFORMATION: Canine pancreatic lipase peptide which is a
      20-mer peptide spanning the canine pancreatic lipase protein cPLP1
      in 10 amino acid sequence overlap.

<400> SEQUENCE: 43

Tyr Lys Val Ala Val Thr Leu Ser Gly Lys Val Thr Gly His Val
1               5                   10                  15

Leu Val Ser Leu
            20

<210> SEQ ID NO 44
<211> LENGTH: 20
<212> TYPE: PRT
<213> ORGANISM: Canis sp.
<220> FEATURE:
<221> NAME/KEY: MISC_FEATURE
<223> OTHER INFORMATION: Canine pancreatic lipase peptide which is a
      20-mer peptide spanning the canine pancreatic lipase protein cPLP1
      in 10 amino acid sequence overlap.

<400> SEQUENCE: 44

Lys Val Thr Gly His Val Leu Val Ser Leu Phe Gly Asn Lys Gly Asn
1               5                   10                  15

Ser Lys Gln Tyr
            20

<210> SEQ ID NO 45
<211> LENGTH: 20
<212> TYPE: PRT
<213> ORGANISM: Canis sp.
<220> FEATURE:
<221> NAME/KEY: MISC_FEATURE
<223> OTHER INFORMATION: Canine pancreatic lipase peptide which is a
      20-mer peptide spanning the canine pancreatic lipase protein cPLP1
      in 10 amino acid sequence overlap.

<400> SEQUENCE: 45

Phe Gly Asn Lys Gly Asn Ser Lys Gln Tyr Glu Ile Phe Lys Gly Thr
1               5                   10                  15

Leu Gln Pro Glu
            20

<210> SEQ ID NO 46
<211> LENGTH: 20
```

```
<212> TYPE: PRT
<213> ORGANISM: Canis sp.
<220> FEATURE:
<221> NAME/KEY: MISC_FEATURE
<223> OTHER INFORMATION: Canine pancreatic lipase peptide which is a
      20-mer peptide spanning the canine pancreatic lipase protein cPLP1
      in 10 amino acid sequence overlap.

<400> SEQUENCE: 46

Glu Ile Phe Lys Gly Thr Leu Gln Pro Glu Ser Thr His Ser Asn Glu
1               5                   10                  15

Phe Asp Ser Asp
            20

<210> SEQ ID NO 47
<211> LENGTH: 20
<212> TYPE: PRT
<213> ORGANISM: Canis sp.
<220> FEATURE:
<221> NAME/KEY: MISC_FEATURE
<223> OTHER INFORMATION: Canine pancreatic lipase peptide which is a
      20-mer peptide spanning the canine pancreatic lipase protein cPLP1
      in 10 amino acid sequence overlap.

<400> SEQUENCE: 47

Ser Thr His Ser Asn Glu Phe Asp Ser Asp Val Glu Val Gly Asp Val
1               5                   10                  15

Gln Lys Val Lys
            20

<210> SEQ ID NO 48
<211> LENGTH: 20
<212> TYPE: PRT
<213> ORGANISM: Canis sp.
<220> FEATURE:
<221> NAME/KEY: MISC_FEATURE
<223> OTHER INFORMATION: Canine pancreatic lipase peptide which is a
      20-mer peptide spanning the canine pancreatic lipase protein cPLP1
      in 10 amino acid sequence overlap.

<400> SEQUENCE: 48

Val Glu Val Gly Asp Val Gln Lys Val Lys Phe Val Trp Tyr Asn Asn
1               5                   10                  15

Val Ile Asn Pro
            20

<210> SEQ ID NO 49
<211> LENGTH: 20
<212> TYPE: PRT
<213> ORGANISM: Canis sp.
<220> FEATURE:
<221> NAME/KEY: MISC_FEATURE
<223> OTHER INFORMATION: Canine pancreatic lipase peptide which is a
      20-mer peptide spanning the canine pancreatic lipase protein cPLP1
      in 10 amino acid sequence overlap.

<400> SEQUENCE: 49

Phe Val Trp Tyr Asn Asn Val Ile Asn Pro Thr Leu Pro Arg Val Gly
1               5                   10                  15

Ala Ser Lys Ile
            20

<210> SEQ ID NO 50
<211> LENGTH: 20
<212> TYPE: PRT
<213> ORGANISM: Canis sp.
<220> FEATURE:
```

-continued

```
<221> NAME/KEY: MISC_FEATURE
<223> OTHER INFORMATION: Canine pancreatic lipase peptide which is a
      20-mer peptide spanning the canine pancreatic lipase protein cPLP1
      in 10 amino acid sequence overlap.

<400> SEQUENCE: 50

Thr Leu Pro Arg Val Gly Ala Ser Lys Ile Thr Val Glu Arg Asn Asp
1               5                   10                  15

Gly Lys Ile Phe
            20

<210> SEQ ID NO 51
<211> LENGTH: 20
<212> TYPE: PRT
<213> ORGANISM: Canis sp.
<220> FEATURE:
<221> NAME/KEY: MISC_FEATURE
<223> OTHER INFORMATION: Canine pancreatic lipase peptide which is a
      20-mer peptide spanning the canine pancreatic lipase protein cPLP1
      in 10 amino acid sequence overlap.

<400> SEQUENCE: 51

Thr Val Glu Arg Asn Asp Gly Lys Ile Phe Asn Phe Cys Ser Lys Glu
1               5                   10                  15

Thr Val Arg Glu
            20

<210> SEQ ID NO 52
<211> LENGTH: 19
<212> TYPE: PRT
<213> ORGANISM: Canis sp.
<220> FEATURE:
<221> NAME/KEY: MISC_FEATURE
<223> OTHER INFORMATION: Canine pancreatic lipase peptide which is a
      20-mer peptide spanning the canine pancreatic lipase protein cPLP1
      in 10 amino acid sequence overlap.

<400> SEQUENCE: 52

Asn Phe Cys Ser Lys Glu Thr Val Arg Glu Asp Ile Leu Leu Thr Leu
1               5                   10                  15

Thr Pro Cys
```